(12) United States Patent
Basu et al.

(10) Patent No.: US 12,426,945 B2
(45) Date of Patent: Sep. 30, 2025

(54) CATHETER WITH THIN-FILM ELECTRODES ON EXPANDABLE MECHANICAL STRUCTURE

(71) Applicant: Biosense Webster (Israel) Ltd., Yokneam (IL)

(72) Inventors: Shubhayu Basu, Anaheim, CA (US); Dustin R. Tobey, San Dimas, CA (US); Pieter E. Van Niekerk, Monrovia, CA (US); Cesar Fuentes-Ortega, Pasadena, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 393 days.

(21) Appl. No.: 16/995,921

(22) Filed: Aug. 18, 2020

(65) Prior Publication Data

US 2021/0077183 A1 Mar. 18, 2021

Related U.S. Application Data

(60) Provisional application No. 62/901,824, filed on Sep. 18, 2019.

(51) Int. Cl.
*A61B 18/14* (2006.01)
*A61B 5/00* (2006.01)
(Continued)

(52) U.S. Cl.
CPC .......... *A61B 18/1492* (2013.01); *A61B 5/287* (2021.01); *A61B 5/6852* (2013.01);
(Continued)

(58) Field of Classification Search
CPC ... A61B 18/1492; A61B 5/287; A61B 5/6852; A61B 5/6853; A61B 2034/2048;
(Continued)

(56) References Cited

U.S. PATENT DOCUMENTS

| 5,404,638 A | 4/1995 | Imran |
| 5,738,096 A | 4/1998 | Ben-Haim |

(Continued)

FOREIGN PATENT DOCUMENTS

| CA | 2471106 A1 | 1/1995 |
| CN | 104470454 B | 6/2018 |

(Continued)

OTHER PUBLICATIONS

U.S. Appl. No. 62/819,738, filed Mar. 18, 2019, by Basu et al., entitled: "Electrode Configurations for Diagnosis of Arrhythmias."
(Continued)

*Primary Examiner* — Eun Hwa Kim
*Assistant Examiner* — Catherine C. Premraj
(74) *Attorney, Agent, or Firm* — FROST BROWN TODD LLP

(57) ABSTRACT

An apparatus includes a catheter and an end effector. At least a portion of the catheter is sized and configured to fit within a lumen of a cardiovascular system. The end effector is positioned at a distal end of the catheter. The end effector includes a panel, a plurality of mapping electrodes positioned on a first surface of the panel, and a plurality of ablation electrodes positioned on the first surface of the panel. The mapping electrodes are configured to sense electrical potentials in tissue contacting the mapping electrodes. The ablation electrodes are operable to ablate tissue contacting the ablation electrodes.

20 Claims, 10 Drawing Sheets

(51) Int. Cl.
  *A61B 5/287* (2021.01)
  *A61B 17/00* (2006.01)
  *A61B 18/00* (2006.01)
  *A61B 34/20* (2016.01)

(52) U.S. Cl.
  CPC .. *A61B 5/6853* (2013.01); *A61B 2017/00199* (2013.01); *A61B 2017/00862* (2013.01); *A61B 2017/00867* (2013.01); *A61B 2018/00077* (2013.01); *A61B 2018/00214* (2013.01); *A61B 2018/00351* (2013.01); *A61B 2018/00577* (2013.01); *A61B 2018/00613* (2013.01); *A61B 2018/00797* (2013.01); *A61B 2018/00815* (2013.01); *A61B 2018/00821* (2013.01); *A61B 2018/1467* (2013.01); *A61B 2034/2048* (2016.02); *A61B 2034/2051* (2016.02); *A61B 2034/2055* (2016.02); *A61B 2034/2063* (2016.02); *A61B 2218/002* (2013.01)

(58) Field of Classification Search
  CPC .... A61B 2034/2051; A61B 2034/2055; A61B 2034/2063; A61B 2017/00199; A61B 2017/00862; A61B 2017/00867; A61B 2018/00077; A61B 2018/00214; A61B 2018/00351; A61B 2018/00577; A61B 2018/00613; A61B 2018/00797; A61B 2018/00815; A61B 2018/00821; A61B 2018/1467; A61B 2218/002
  See application file for complete search history.

(56) References Cited

U.S. PATENT DOCUMENTS

| | | | |
|---|---|---|---|
| 5,827,273 | A | 10/1998 | Edwards |
| 5,846,196 | A * | 12/1998 | Siekmeyer ........... A61B 5/6853 606/41 |
| 6,315,776 | B1 | 11/2001 | Edwards et al. |
| 6,325,972 | B1 | 12/2001 | Jacobs et al. |
| 6,365,102 | B1 | 4/2002 | Wu et al. |
| 6,447,719 | B1 | 9/2002 | Agamohamadi et al. |
| 6,852,277 | B2 | 2/2005 | Platt, Jr. et al. |
| 6,852,279 | B2 | 2/2005 | Williams et al. |
| 6,939,519 | B2 | 9/2005 | Agamohamadi et al. |
| 8,295,902 | B2 | 10/2012 | Salahieh et al. |
| 8,956,353 | B2 | 2/2015 | Govari et al. |
| 9,131,836 | B2 | 9/2015 | Huszar et al. |
| 9,186,060 | B2 | 11/2015 | De Graff et al. |
| 9,314,299 | B2 | 4/2016 | Fang |
| 9,370,311 | B2 | 6/2016 | Stewart et al. |
| 9,480,416 | B2 | 11/2016 | Govari et al. |
| 9,801,585 | B2 | 10/2017 | Shah et al. |
| 9,848,795 | B2 | 12/2017 | Marecki et al. |
| 9,907,480 | B2 | 3/2018 | Basu et al. |
| 10,061,198 | B2 | 8/2018 | Lima De Miranda |
| 10,105,179 | B2 | 10/2018 | Harlev et al. |
| 10,130,442 | B2 | 11/2018 | Dor et al. |
| 10,561,753 | B2 | 2/2020 | Thompson et al. |
| 10,575,743 | B2 | 3/2020 | Basu et al. |
| 10,660,700 | B2 | 5/2020 | Beeckler et al. |
| 10,702,177 | B2 | 7/2020 | Aujla |
| 10,743,932 | B2 | 8/2020 | Gallardo et al. |
| 10,898,139 | B2 | 1/2021 | Guta et al. |
| 11,026,746 | B2 | 6/2021 | Townley et al. |
| 2015/0351652 | A1 * | 12/2015 | Marecki ............ A61B 18/1492 29/829 |
| 2017/0071543 | A1 | 3/2017 | Basu et al. |
| 2018/0071017 | A1 * | 3/2018 | Bar-Tal ............. A61B 18/1492 |
| 2018/0133460 | A1 * | 5/2018 | Townley ............. A61N 1/0546 |
| 2018/0325587 | A1 | 11/2018 | Buelna |
| 2019/0159835 | A1 | 5/2019 | Ibrahim |

FOREIGN PATENT DOCUMENTS

| | | |
|---|---|---|
| DE | 102017130152 B3 | 1/2019 |
| WO | 1999/008614 A1 | 2/1999 |
| WO | WO 00/066021 A1 | 11/2000 |
| WO | WO 2011/143468 A2 | 11/2011 |
| WO | WO 2015/117908 A1 | 8/2015 |
| WO | WO 2016/123390 A1 | 8/2016 |
| WO | WO 2019/036653 A2 | 2/2019 |
| WO | 2021/053483 A1 | 3/2021 |

OTHER PUBLICATIONS

U.S. Appl. No. 62/901,824, filed Sep. 18, 2019, by Basu et al., entitled: "Catheter With Thin-Film Electrodes on Expandable Mechanical Structure."
International Search Report and Written Opinion dated Apr. 16, 2021 for Application No. PCT/IB2020/058355, 16 pgs.
European Communication dated Nov. 14, 2023, for Application No. 20785601.4, 6 pages.
Japanese Notification of Reasons for Refusal dated Mar. 5, 2024, for Application No. 2022-517429, 6 pages.
Chinese Office Action, The First Office Action and First Search, dated Aug. 15, 2024 for Application No. CN 202080065607.1, 11 pgs.
Chinese Office Action, The Second Office Action, dated Dec. 5, 2024 for Application No. CN 202080065607.1, 4 pgs.
European Search Report and Written Opinion dated Feb. 13, 2025 for Application No. EP 25151816.3, 11 pgs.
Invitation to Pay Additional Fees and, Where Applicable, Protest Fee dated Jan. 12, 2021 for International Application No. PCT/IB2020/058355, 10 pgs.
U.S. Food & Drug Administration, "FDA-Cleared Sterilants and High Level Disinfectants with General Claims for Processing Reusable Medical and Dental Devices—Mar. 2015," downloaded Jun. 21, 2019 from https://www.fda.gov/medical-devices/reprocessing-reusable-medical-devices-information-manufacturers/fda-cleared-sterilants-and-high-level•disinfectants-general-claims-processing-reusable-medical-and, 7 pgs.

* cited by examiner

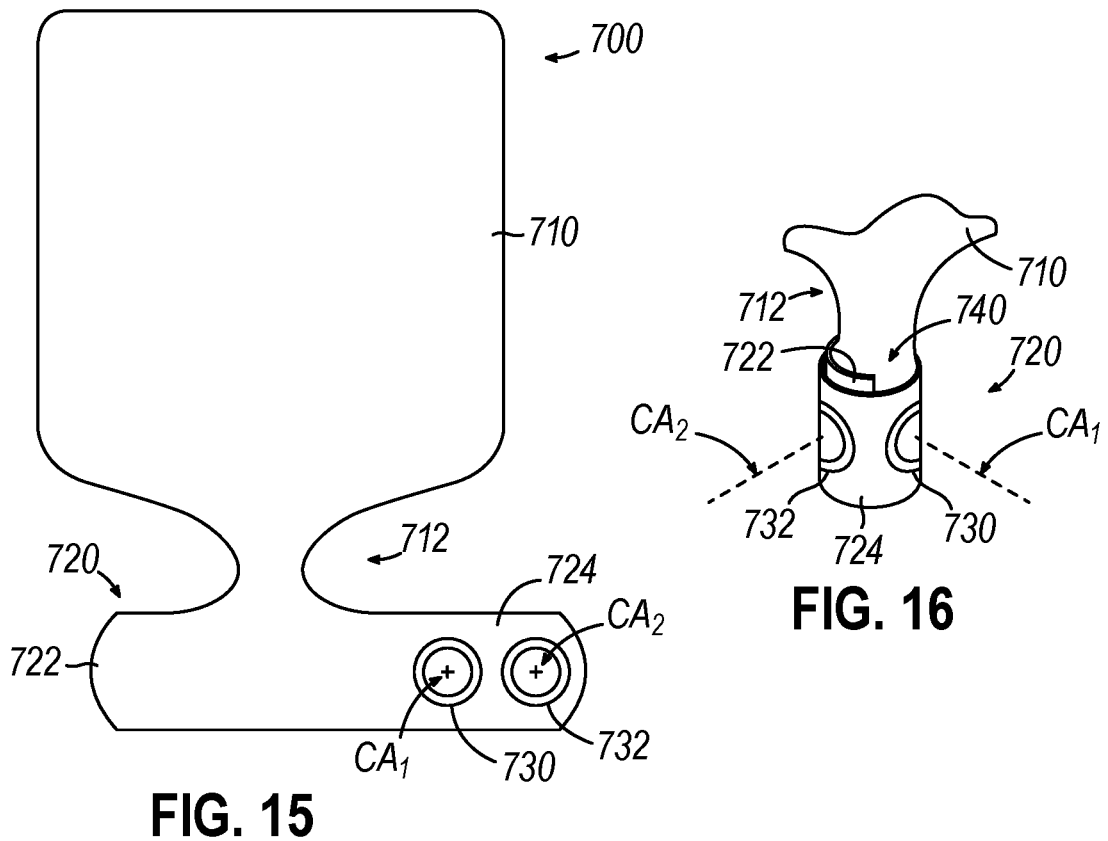
FIG. 15
FIG. 16
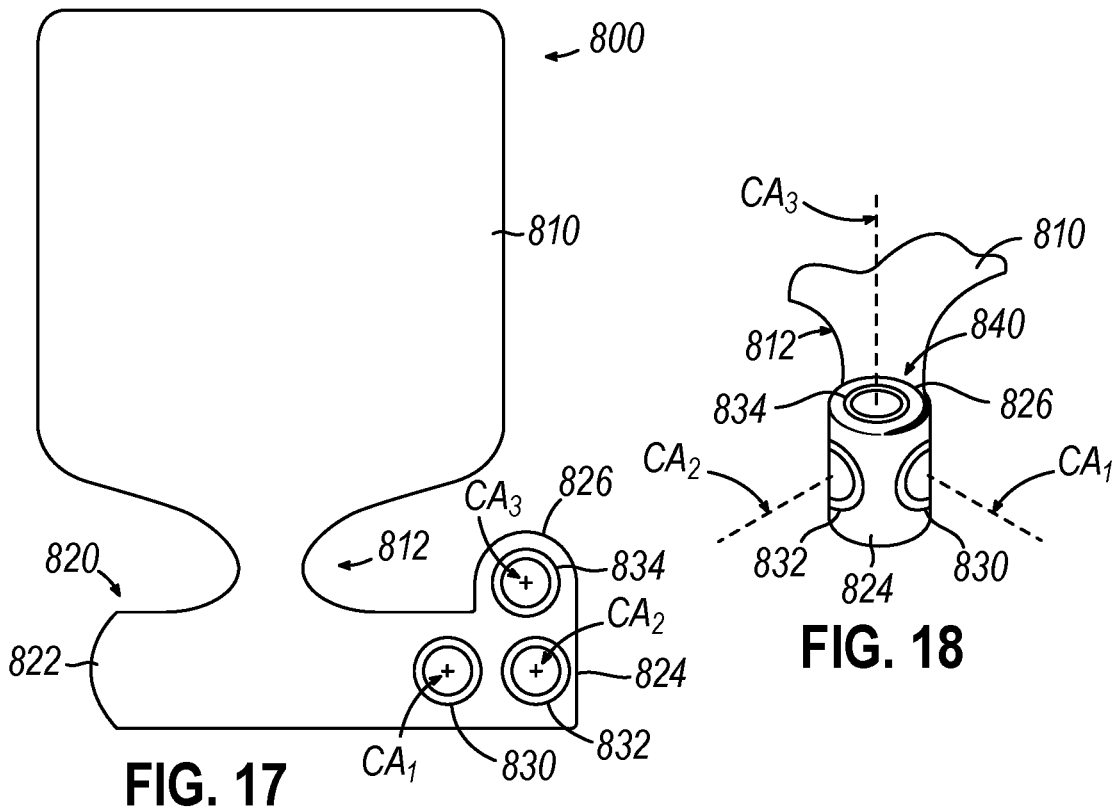
FIG. 17
FIG. 18

CATHETER WITH THIN-FILM ELECTRODES ON EXPANDABLE MECHANICAL STRUCTURE

PRIORITY

This application claims priority to U.S. Provisional Pat. App. No. 62/901,824, entitled "Catheter with Thin-Film Electrodes on Expandable Mechanical Structure," filed Sep. 18, 2019, the disclosure of which is incorporated by reference herein, in its entirety.

BACKGROUND

Cardiac arrhythmias, such as atrial fibrillation, occur when regions of cardiac tissue abnormally conduct electric signals. Procedures for treating arrhythmia include surgically disrupting the conducting pathway for such signals. By selectively ablating cardiac tissue by application of energy (e.g., alternating-current or direct-current energy), it may be possible to cease or modify the propagation of unwanted electrical signals from one portion of the heart to another. The ablation process may provide a barrier to unwanted electrical pathways by creating electrically insulative lesions or scar tissue that effectively block communication of aberrant electrical signals across the tissue.

In some procedures, a catheter with one or more electrodes may be used to provide ablation within the cardiovascular system. The catheter may be inserted into a major vein or artery (e.g., the femoral artery) and then advanced to position the electrodes within the heart or in a cardiovascular structure adjacent to the heart (e.g., the pulmonary vein). The electrodes may be placed in contact with cardiac tissue or other vascular tissue and then activated with electrical energy to thereby ablate the contacted tissue. In some cases, the electrodes may be bipolar. In some other cases, a monopolar electrode may be used in conjunction with a ground pad or other reference electrode that is in contact with the patient.

Examples of ablation catheters are described in U.S. Pub. No. 2013/0030426, entitled "Integrated Ablation System using Catheter with Multiple Irrigation Lumens," published Jan. 31, 2013, the disclosure of which is incorporated by reference herein, in its entirety; U.S. Pub. No. 2017/0312022, entitled "Irrigated Balloon Catheter with Flexible Circuit Electrode Assembly," published Nov. 2, 2017, the disclosure of which is incorporated by reference herein, in its entirety; U.S. Pub. No. 2018/0071017, entitled "Ablation Catheter with a Flexible Printed Circuit Board," published Mar. 15, 2018, the disclosure of which is incorporated by reference herein, in its entirety; U.S. Pub. No. 2018/0056038, entitled "Catheter with Bipole Electrode Spacer and Related Methods," published Mar. 1, 2018, the disclosure of which is incorporated by reference herein, in its entirety; U.S. Pat. No. 10,130,422, entitled "Catheter with Soft Distal Tip for Mapping and Ablating Tubular Region," issued Nov. 20, 2018, the disclosure of which is incorporated by reference herein, in its entirety; U.S. Pat. No. 8,956,353, entitled "Electrode Irrigation Using Micro-Jets," issued Feb. 17, 2015, the disclosure of which is incorporated by reference herein, in its entirety; and U.S. Pat. No. 9,801,585, entitled "Electrocardiogram Noise Reduction," issued Oct. 31, 2017, the disclosure of which is incorporated by reference herein, in its entirety.

Some catheter ablation procedures may be performed after using electrophysiology (EP) mapping to identify tissue regions that should be targeted for ablation. Such EP mapping may include the use of sensing electrodes on a catheter (e.g., the same catheter that is used to perform the ablation or a dedicated mapping catheter). Such sensing electrodes may monitor electrical signals emanating from conductive endocardial tissues to pinpoint the location of aberrant conductive tissue sites that are responsible for the arrhythmia. Examples of an EP mapping system are described in U.S. Pat. No. 5,738,096, entitled "Cardiac Electromechanics," issued Apr. 14, 1998, the disclosure of which is incorporated by reference herein, in its entirety. Examples of EP mapping catheters are described in U.S. Pat. No. 9,907,480, entitled "Catheter Spine Assembly with Closely-Spaced Bipole Microelectrodes," issued Mar. 6, 2018, the disclosure of which is incorporated by reference herein, in its entirety; U.S. Pat. No. 10,130,422, entitled "Catheter with Soft Distal Tip for Mapping and Ablating Tubular Region," issued Nov. 20, 2018, the disclosure of which is incorporated by reference herein, in its entirety; and U.S. Pub. No. 2018/0056038, entitled "Catheter with Bipole Electrode Spacer and Related Methods," published Mar. 1, 2018, the disclosure of which is incorporated by reference herein, in its entirety.

In addition to using EP mapping, some catheter ablation procedures may be performed using an image guided surgery (IGS) system. The IGS system may enable the physician to visually track the location of the catheter within the patient, in relation to images of anatomical structures within the patient, in real time. Some systems may provide a combination of EP mapping and IGS functionalities, including the CARTO 3® system by Biosense Webster, Inc. of Irvine, Calif. Examples of catheters that are configured for use with an IGS system are disclosed in U.S. Pat. No. 9,480,416, entitled "Signal Transmission Using Catheter Braid Wires," issued Nov. 1, 2016, the disclosure of which is incorporated by reference herein, in its entirety; and various other references that are cited herein.

While several catheter systems and methods have been made and used, it is believed that no one prior to the inventors has made or used the invention described in the appended claims.

BRIEF DESCRIPTION OF THE DRAWINGS

The drawings and detailed description that follow are intended to be merely illustrative and are not intended to limit the scope of the invention as contemplated by the inventors.

FIG. 15 depicts a depicts a top plan view of another example of a panel component that may be incorporated into any of the panel assemblies described herein;

FIG. 16 depicts a perspective view of a proximal portion of the panel component of FIG. 15 in a rolled configuration;

FIG. 17 depicts a depicts a top plan view of another example of a panel component that may be incorporated into any of the panel assemblies described herein;

FIG. 18 depicts a perspective view of a proximal portion of the panel component of FIG. 17 in a rolled configuration;

DETAILED DESCRIPTION FOR MODES OF CARRYING OUT THE INVENTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%. In addition, as used herein, the terms "patient," "host," "user," and "subject" refer to any human or animal subject and are not intended to limit the systems or methods to human use, although use of the subject invention in a human patient represents a preferred embodiment.

I. Overview of Example of a Catheter System

Figure 1:
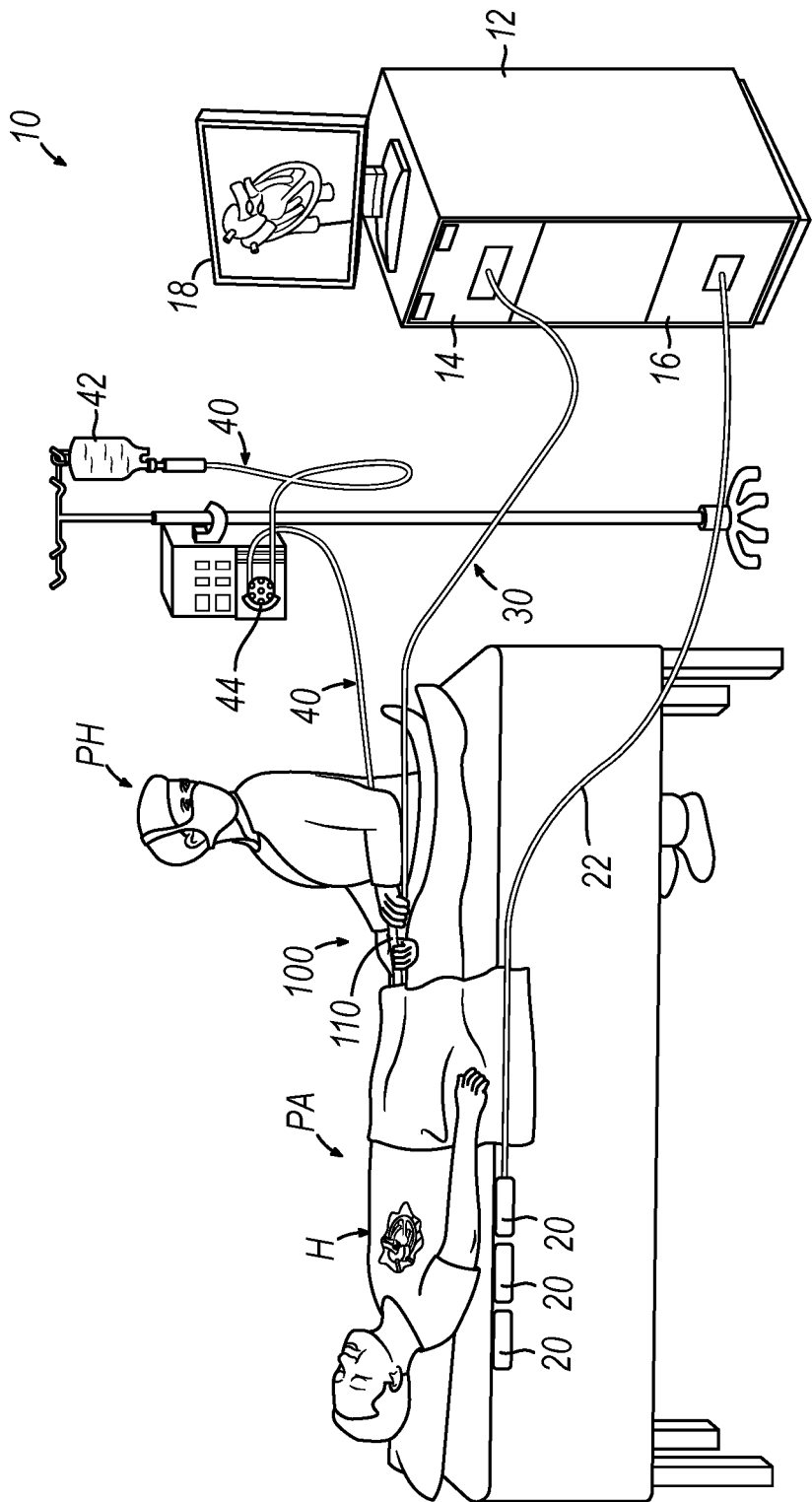
FIG. 1 depicts a schematic view of a medical procedure in which a catheter of a catheter assembly is inserted in a patient.
Figure 2A:
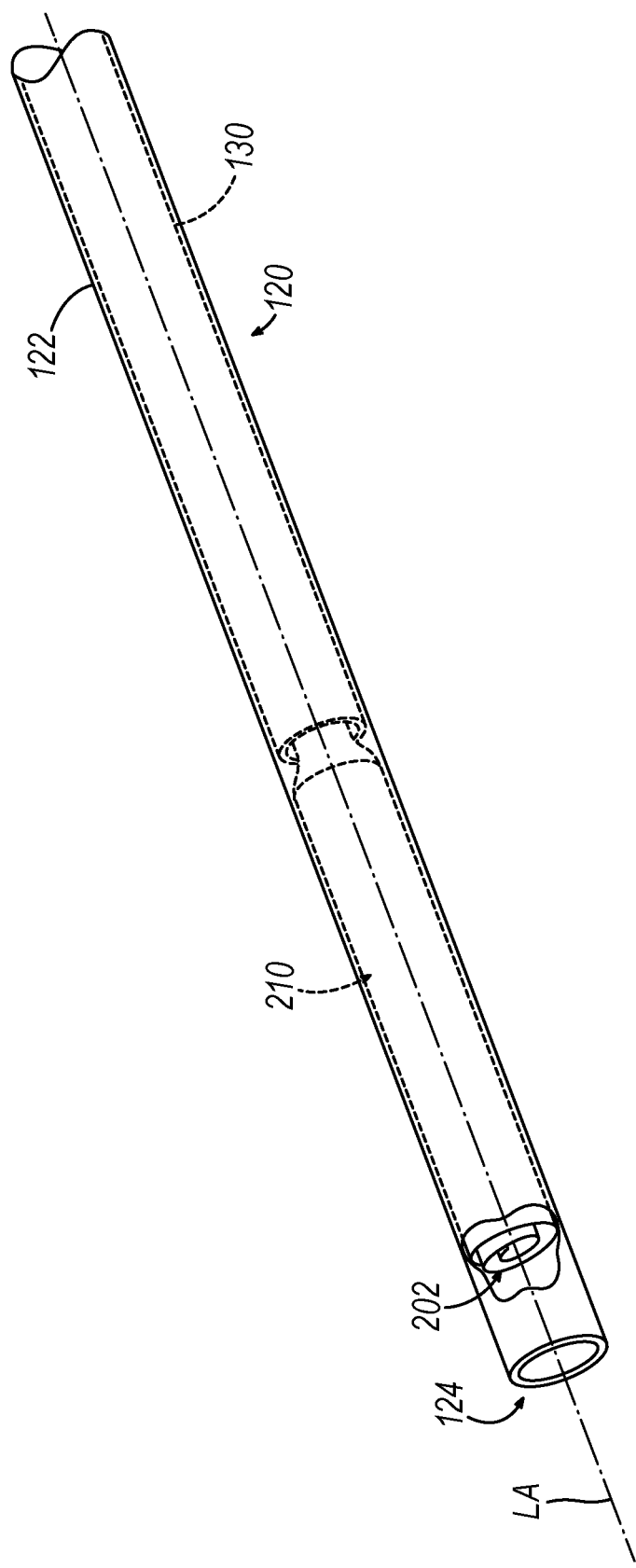
FIG. 2A depicts a perspective view of a distal portion of the catheter assembly of FIG. 1, with an end effector in a non-expanded state.
Figure 2B:
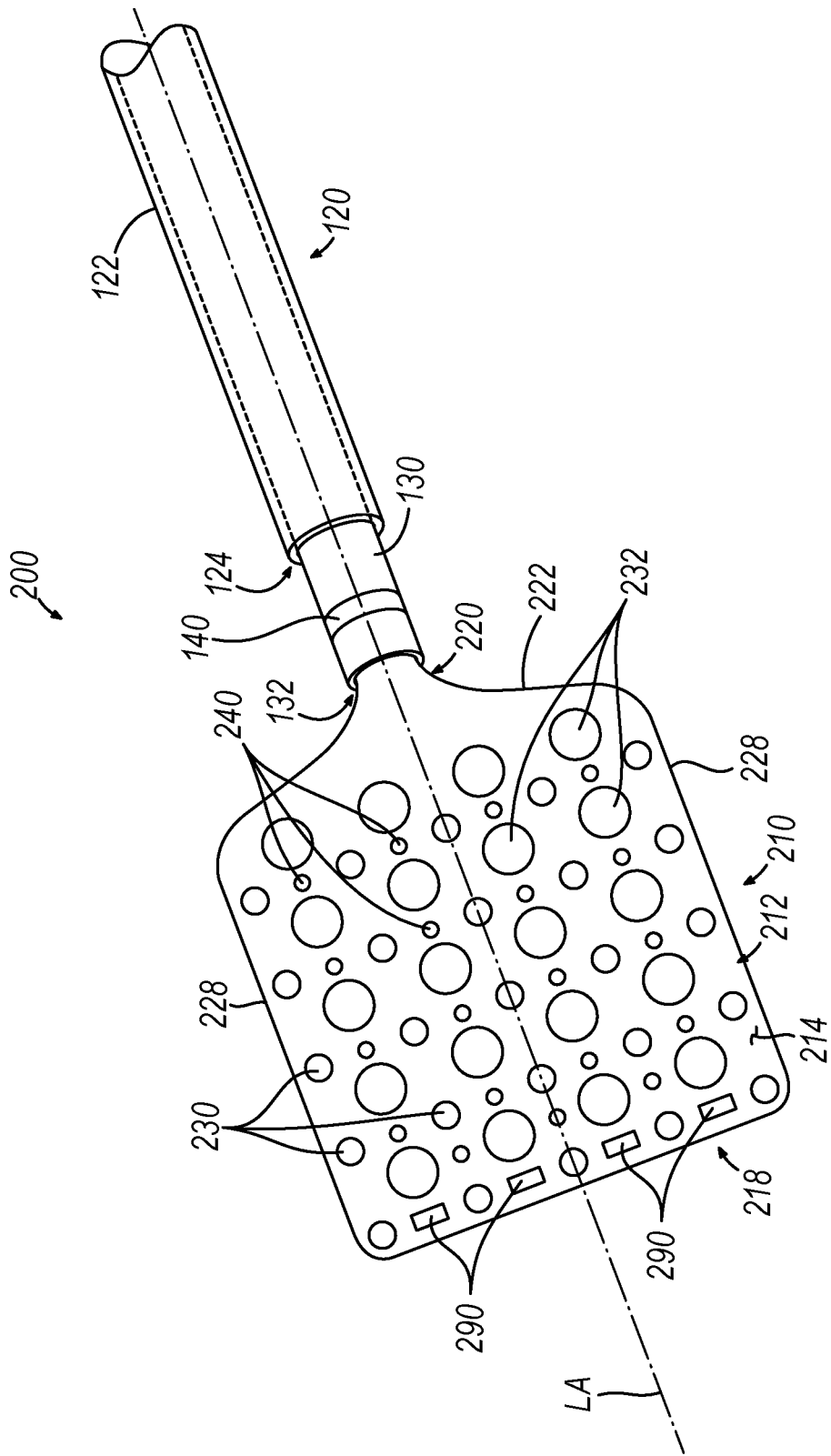
FIG. 2B depicts perspective view of a distal portion of the catheter assembly of FIG. 1, with the end effector in an expanded state.

FIG. 1 shows an example of a medical procedure and associated components of a cardiac mapping and ablation system. In particular, FIG. 1 shows a physician (PH) grasping a handle (110) of a catheter assembly (100), with an end effector (200) of a flexible catheter (120) (shown in FIGS. 2A-2B but not shown in FIG. 1) of catheter assembly (100) disposed in a patient (PA) to map or ablate tissue in or near the heart (H) of the patient (PA). As shown in FIGS. 2A-2B, catheter (120) includes an outer sheath (122) and an inner shaft (130), with end effector (200) being disposed a distal end (132) of inner shaft (130). Catheter assembly (100) is coupled with a guidance and drive system (10) via a cable (30). Catheter assembly (100) is also coupled with a fluid source (42) via a fluid conduit (40), though this is merely optional. A set of field generators (20) are positioned underneath the patient (PA) and are also coupled with guidance and drive system (10) via a cable (22).

Guidance and drive system (10) of the present example includes a console (12) and a display (18). Console (12) includes a first driver module (14) and a second driver module (16). First driver module (14) is coupled with catheter assembly (100) via cable (30). In some variations, first driver module (14) is operable to receive EP mapping signals obtained via electrodes (230) of end effector (200) as described in greater detail below. Console (12) includes a processor (not shown) that processes such EP mapping signals and thereby provides EP mapping as is known in the art. In addition, or in the alternative, first driver module (14) may be operable to provide electrical power to electrodes (232) of end effector (200) to thereby ablate tissue. In some versions, first driver module (14) is also operable to receive position indicative signals from one or more position sensors (290) in end effector (200), as will be described in greater detail below. In such versions, the processor of console (12) is also operable to process the position indicative signals from a position sensor (290) to thereby determine the position of the end effector (200) of catheter (120) within the patient (PA).

Second driver module (16) is coupled with field generators (20) via cable (22). Second driver module (16) is operable to activate field generators (20) to generate an alternating magnetic field around the heart (H) of the patient (PA). For instance, field generators (20) may include coils that generate alternating magnetic fields in a predetermined working volume that contains the heart (H).

Display (18) is coupled with the processor of console (12) and is operable to render images of patient anatomy. Such images may be based on a set of preoperatively or intraoperatively obtained images (e.g., a CT or MRI scan, 3-D map, etc.). The views of patient anatomy provided through display (18) may also change dynamically based on signals from position sensors (290) of end effector (200). For instance, as end effector (200) of catheter (120) moves within the patient (PA), the corresponding position data from position sensors (290) may cause the processor of console (12) to update the patient anatomy views in display (18) in real time to depict the regions of patient anatomy around end effector (200) as end effector (200) moves within the patient (PA). Moreover, the processor of console (12) may drive display (18) to show locations of aberrant conductive tissue sites, as detected via EP mapping with end effector (200). By way of example only, the processor of console (12) may drive display (18) to superimpose the locations of aberrant conductive tissue sites on the images of the patient's anatomy, such as by superimposing an illuminated dot, a crosshair, or some other form of visual indication of aberrant conductive tissue sites.

The processor of console (12) may also drive display (18) to superimpose the current location of end effector (200) on the images of the patient's anatomy, such as by superimposing an illuminated dot, a crosshair, a graphical representation of end effector (200), or some other form of visual indication. Such a superimposed visual indication may also move within the images of the patient anatomy on display (18) in real time as the physician moves end effector (200) within the patient (PA), thereby providing real-time visual feedback to the operator about the position of end effector (200) within the patient (PA) as end effector (200) moves within the patient (PA). The images provided through display (18) may thus effectively provide a video tracking the position of end effector (200) within a patient (PA), without necessarily having any optical instrumentation (i.e., cameras) viewing end effector (200). In the same view, display (18) may simultaneously visually indicate the locations of aberrant conductive tissue sites detected through the EP mapping as described herein. The physician (PH) may thus view display (18) to observe the real time positioning of end effector (200) in relation to the mapped aberrant conductive tissue sites and in relation to images of the adjacent anatomical structures in the patient (PA).

Fluid source (42) of the present example includes a bag containing saline or some other suitable irrigation fluid. Conduit (40) includes a flexible tube that is further coupled with a pump (44), which is operable to selectively drive fluid from fluid source (42) to catheter assembly (100). In some variations, conduit (40), fluid source (42), and pump (44) are omitted entirely. In versions where these components are included, end effector (200) may be configured to communicate irrigation fluid from fluid source (42) to the target site in the patient. Such irrigation may be provided in accordance with the teachings of any of the various patent references cited herein; or in any other suitable fashion as will be apparent to those skilled in the art in view of the teachings herein.

FIGS. 2A-2B show catheter (120) in greater detail. As shown, outer sheath (122) is configured to translate relative to end effector (200) and relative to inner shaft (130) between a distal position (FIG. 2A) and a proximal position (FIG. 2B). When outer sheath (122) is in the distal position as shown in FIG. 2A, the distal end (124) of outer sheath (122) is positioned distally relative to the distal end (202) of end effector (200), such that end effector (200) is fully contained within the interior of outer sheath (122). In some versions, end effector (200) is configured to have a size less than or equal to approximately 6 French when in the non-expanded configuration shown in FIG. 2A. When outer sheath (122) is in the proximal position as shown in FIG. 2B, distal end (124) of outer sheath (122) is positioned proximally relative to end effector (200), such that end effector (200) and a distal portion of inner shaft (130) are exposed relative to outer sheath (122). As shown in the transition from FIG. 2A to FIG. 2B, and as will be described in greater detail below, end effector (200) is operable to transition from a non-expanded state to an expanded state after being exposed by outer sheath (122).

II. Example of an End Effector with Expandable Panel Assembly

As shown in FIG. 2B, end effector (200) of the present example is formed by a panel assembly (210) and an exposed distal portion of inner shaft (130). As shown in FIG. 2A, panel assembly (210) is configured to be in a rolled state to thereby achieve a non-expanded configuration within the hollow interior of outer sheath (122). In this example, panel assembly (210) is rolled about the central longitudinal axis (LA) of end effector (200) and catheter (120) when panel assembly (210) is contained within outer sheath (122). However, once panel assembly (210) is exposed by the proximally retracted outer sheath (122) as shown in FIG. 2B, panel assembly (210) unfurls and resiliently returns to a flat state. In order to provide a resilient bias toward a flattened configuration, panel assembly (210) may incorporate a resilient material as will be described in greater detail below. In the expanded, flat state (or flattened configuration), panel assembly (210) is generally planar. By way of example only, in the expanded, flat state, a distal portion (212) of panel assembly (210) may have a length from approximately 2 cm to approximately 3 cm; and a width from approximately 1 cm to approximately 2 cm.

During use of catheter assembly (100), outer sheath (122) may be kept in the distal position as shown in FIG. 2A as catheter (120) is being advanced into the patient (PA). Once the distal portion of catheter (120) reaches the targeted anatomical region, outer sheath (122) may be retracted proximally relative to end effector (200) and inner shaft (130) to achieve the state shown in FIG. 2B. Alternatively, once the distal portion of catheter (120) reaches the targeted anatomical region, end effector (200) and inner shaft (130) may be advanced distally relative to outer sheath (122) to achieve the state shown in FIG. 2B.

After end effector (200) has been used to provide EP mapping or ablation as described herein, and before end effector (200) is withdrawn from the patient, outer sheath (122) may be returned to the distal position shown in FIG. 2A to cover end effector (200) during withdrawal of catheter (120) from the patient (PA). When outer sheath (122) is advanced distally relative to end effector (200) and relative to inner sheath (130) (or when end effector (200) and inner sheath (130) are retracted proximally relative to outer sheath (122)), distal end (124) of outer sheath (120) may interact with proximally facing edges (222) at the proximal end (220) of panel assembly (210).

Figure 11:
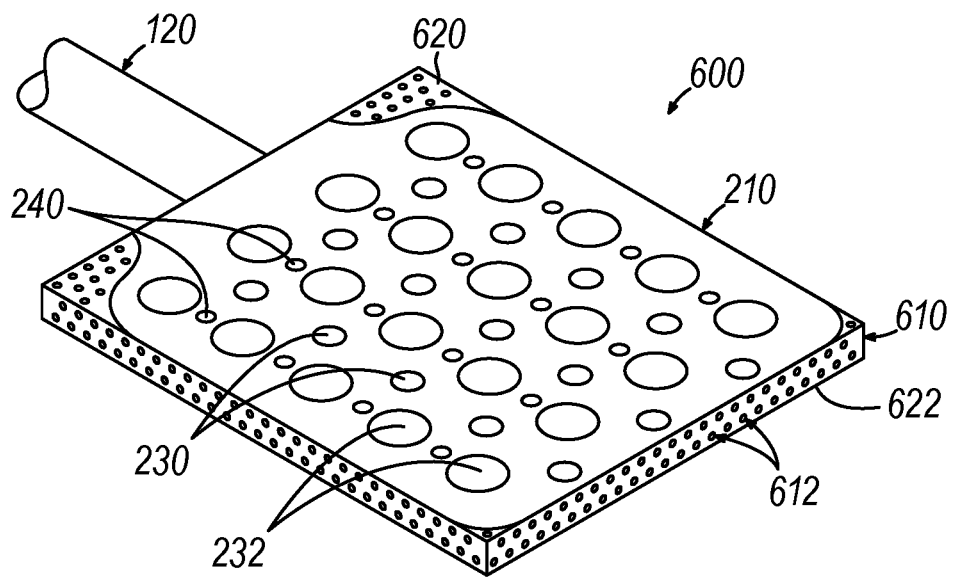
FIG. 11 depicts a perspective view of another example of an end effector that may be incorporated into the catheter assembly of FIG. 1.
Figure 12:
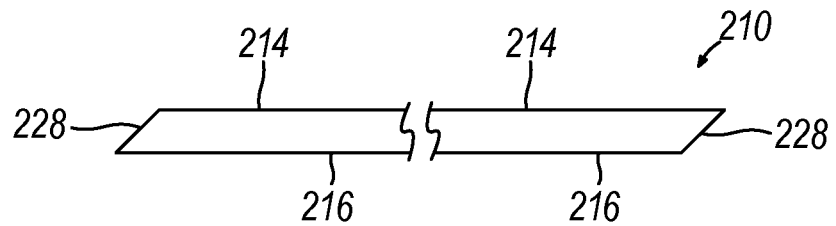
FIG. 12 depicts a schematic end view of an example of a panel assembly with lateral edges that are angled across the thickness of the panel assembly.

In the present example, edges (222) are tapered to provide a camming interaction with distal end (124) of outer sheath (120), to thereby promote a return of panel assembly (210) to the rolled state shown in FIG. 2A as outer sheath (122) is advanced distally relative to end effector (200). In some versions, edges (222) may also include a three-dimensional curved profile that further promotes a return of panel assembly (210) to the rolled state shown in FIG. 2A as outer sheath (122) is advanced distally relative to end effector (200). For instance, panel assembly (210) may have a preformed concave curvature in the region of panel assembly (210) near edges (222), with the concave curvature being configured to define camming surfaces that engage distal end (124) of outer sheath (122) to thereby urge panel assembly (210) from the flattened configuration of FIG. 2B to the rolled (or otherwise non-expanded) configuration of FIG. 2B as outer sheath (122) is transitioned from the proximal position to the distal position. In addition to, or as an alternative to, having the features described above, panel assembly (210) may be configured such that the longitudinally extending lateral edges (228) of panel assembly (210) have an angled profile through the thickness of panel assembly (210). In some such versions, and as shown in FIG. 11, the angle of one lateral edge (228) is a reverse of the angle of the other lateral edge (228). Such an opposing angle configuration may promote lateral edges (228) sliding off of each other if they come into contact as panel assembly (210) is transitioning to the rolled (or otherwise non-expanded) configuration of FIG. 2B as outer sheath (122) is transitioned from the proximal position to the distal position. This angled profile may be defined in a thin film body that defines panel assembly (210); may be constructed as separate bumpers or other structures that are secured to a thin film body that defines panel assembly (210); or may be otherwise constructed.

Figure 13:
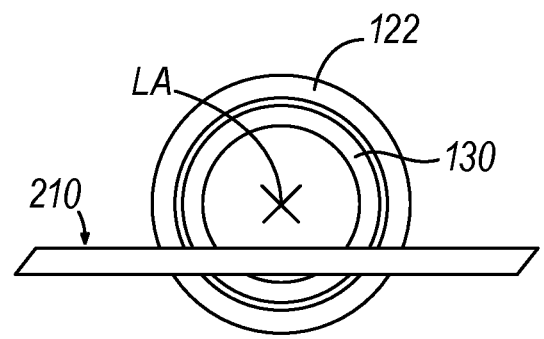
FIG. 13 depicts a schematic end view of an example of a panel assembly that is laterally offset from a longitudinal axis of a shaft assembly.
Figure 14:
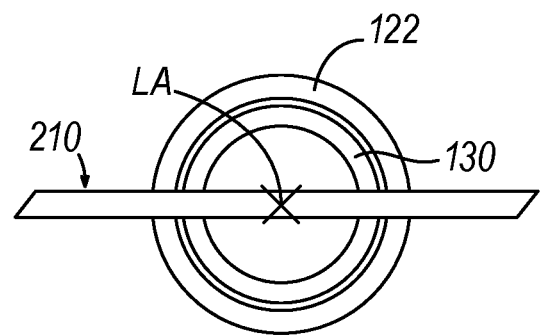
FIG. 14 depicts a schematic end view of an example of a panel assembly that is aligned with a longitudinal axis of a shaft assembly.

Also, in some versions, panel assembly (210) is positioned to be laterally offset from (yet parallel with) the longitudinal axis (LA) of outer sheath (122) as shown in FIG. 13. By being positioned with such an offset, edges (222) may further cooperate with distal end (124) of outer sheath (122) to urge panel assembly (210) from the flattened configuration of FIG. 2B to the rolled (or otherwise non-expanded) configuration of FIG. 2B as outer sheath (122) is transitioned from the proximal position to the distal position. However, other versions may provide panel assembly (210) in alignment with the longitudinal axis (LA) of outer sheath (122) as shown in FIG. 14; and panel assembly may still transition from the flattened configuration of FIG. 2B to the rolled (or otherwise non-expanded) configuration of FIG. 2B as outer sheath (122) is transitioned from the proximal position to the distal position. In any case, once outer sheath (122) is back to the distal position of FIG. 2A with end effector (200) contained within outer sheath (122), catheter (120) may be removed from the patient (PA).

Figure 4:
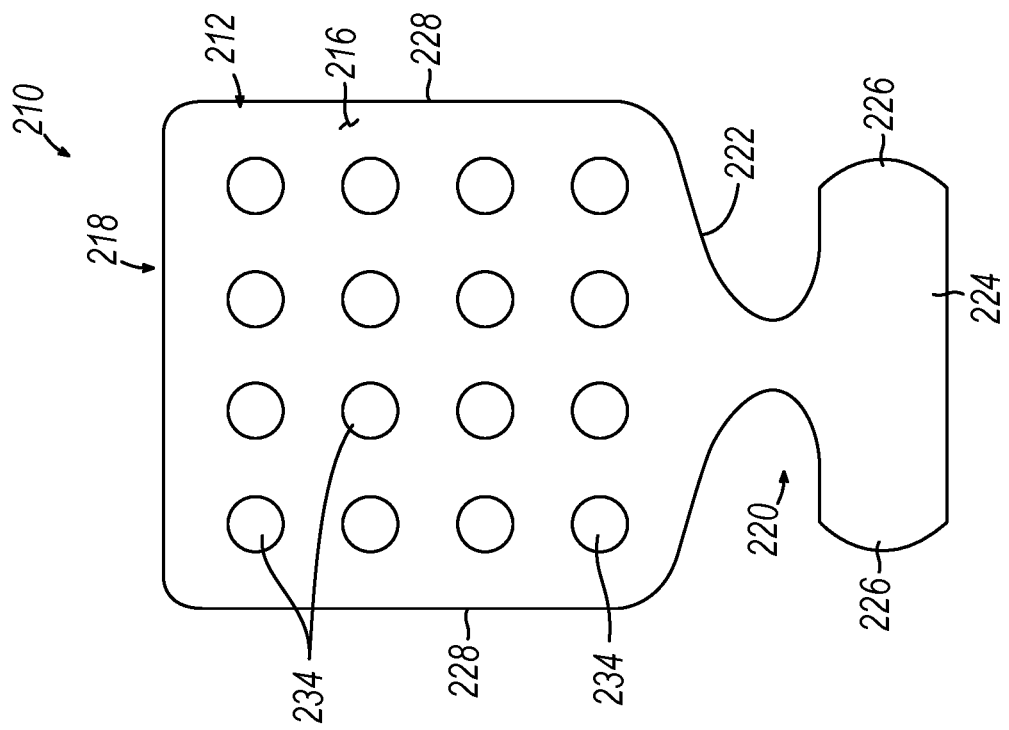
FIG. 4 depicts a bottom plan view of the panel assembly of FIG. 3.
Figure 3:
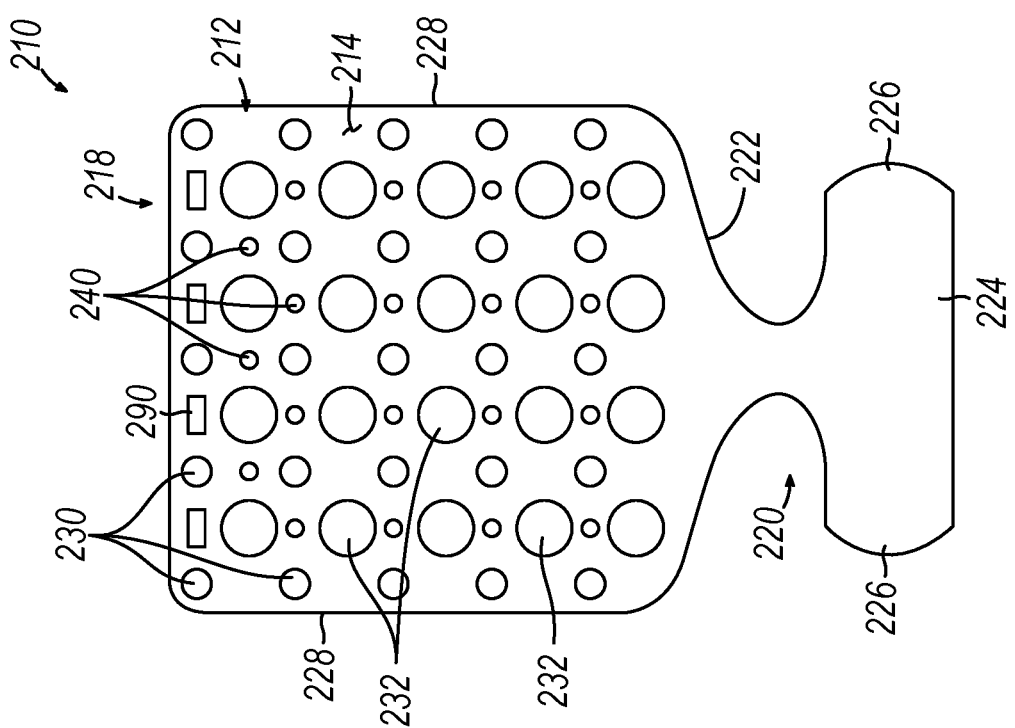
FIG. 3 depicts a top plan view of a panel assembly of the end effector of FIG. 2A.
Figure 5:
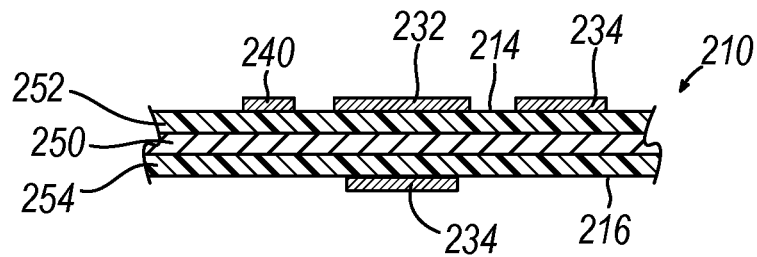
FIG. 5 depicts a cross-sectional view of the panel assembly of FIG. 3.

As shown in FIGS. 3-5, panel assembly (210) of this example includes a distal portion (212) having a distal end (218), a proximal portion (220), a first surface (214), and a second surface (216) opposing first surface (214). Distal portion (212) of the present example is generally square-shaped, though distal portion (212) may instead be shaped like any other kind of rectangle or have any other suitable kind of shape. First surface (214) includes a plurality of mapping electrodes (230), a plurality of ablation electrodes (232), a plurality of temperature sensors (240), and a plurality of position sensors (290). Second surface (216) includes a plurality of reference electrodes (234). Proximal portion (220) includes proximally facing edges (222), as noted above, and a tab portion (224). Tab portion (224) includes a pair of outwardly extending ears (226). Tab portion (224) is configured to be rolled and inserted into distal end (132) of inner shaft (130); and then be fixedly secured in inner shaft (130) as shown in FIG. 2B. By way of example only, tab portion (224) may be secured to inner shaft (130) using an adhesive or using any other suitable techniques as will be apparent to those skilled in the art in view of the teachings herein. In addition to providing a structure by which to secure panel assembly (210) to inner shaft (130), tab portion (224) may provide sufficient surface area for electrical connections between wires (not shown) in inner shaft (130) and various electrical features (e.g., mapping electrodes (230), ablation electrodes (232), temperature sensors (240), position sensors (290), and reference electrodes (234), etc.) on panel assembly (210).

In some versions, distal end (132) of inner shaft (130) includes an opening that is in fluid communication with fluid source (42) via a fluid conduit (40). In such versions, inner shaft (130) may expel irrigation fluid out through distal end (132) to the targeted site within the patient (PA). The rolled configuration of tab portion (224) at proximal portion (220) of panel assembly (210) may readily permit such fluid communication out through distal end (132). Alternatively, irrigation fluid may be communicated to the target site in the patient (PA) in any other suitable fashion. As yet another alternative, irrigation fluid may be omitted in some versions.

Mapping electrodes (230) are configured to provide EP mapping by contacting tissue and picking up potentials from the contacted tissue (e.g., to provide an electrocardiogram signal). In some versions, mapping electrodes (230) cooperate in bipolar pairs during such mapping procedures. Thus, pair of mapping electrodes (230) may be considered as collectively forming a single "sensor." Each mapping electrode (230) may be coupled with a corresponding trace (not shown) or other electrical conduit, thereby enabling signals picked up by mapping electrodes (230) to be communicated back through electrical conduits (not shown) in catheter (120) to console (12), which may process the signals to provide EP mapping to thereby identify locations of aberrant electrical activity within the cardiac anatomy. This may in turn allow the physician (PH) to identify the most appropriate regions of cardiac tissue to ablate (e.g., with electrical energy, cryoablation, etc.), to thereby prevent or at least reduce the communication of aberrant electrical activity across the cardiac tissue.

In the present example, mapping electrodes (230) are arranged in a grid or matrix across first surface (214) of panel assembly (210). By way of further example only, mapping electrodes (230) may be spaced and arranged in accordance with at least some of the teachings of U.S. Provisional Patent App. No. 62/819,738, entitled "Electrode Configurations for Diagnosis of Arryhtmias," filed Mar. 18, 2019, the disclosure of which is incorporated by reference herein in its entirety. For instance, mapping electrodes (230) may be spaced and arranged in accordance with FIGS. 13A, 13B, 13C, and 13D of U.S. Provisional Patent App. No. 62/819,738.

As shown in FIGS. 2B-3, ablation electrodes (232) are larger than mapping electrodes (230) in this example. Ablation electrodes (232) may be used to apply electrical energy to tissue that is in contact with electrodes (232), to thereby ablate the tissue. As used herein, the term "ablate" is intended to cover either radio-frequency ablation or irreversible electroporation. Each ablation electrode (230) may be coupled with a corresponding trace (not shown) or other electrical conduit, thereby enabling console (12) to communicate electrical energy through electrical conduits (not shown) in catheter (120) to the traces or other conduits of to reach ablation electrodes (232). In some scenarios, only one, only two, or some other relatively small number of ablation electrodes (232) would be activated to apply electrical energy to tissue at any given moment. In the present example, ablation electrodes (232) are arranged in a grid or matrix across first surface (214) of panel assembly (210). This grid or matrix of ablation electrodes (232) is offset from the grid or matrix of mapping electrodes (230). As with mapping electrodes (230), the number and positioning of ablation electrodes (232) as shown in FIGS. 2B-3 is merely illustrative. Any other suitable number or positioning may be used for ablation electrodes (232). As yet another merely illustrative variation, ablation electrodes (232) may be omitted from end effector (200). In some such variations, mapping electrodes (230) are still included on end effector (200).

As also shown in FIGS. 2B-3, temperature sensors (240) are arranged in a grid or matrix across first surface (214) of panel assembly (210). This grid or matrix of temperature sensors (240) is offset from the grids or matrices of mapping electrodes (230) and ablation electrodes (232). As with mapping electrodes (230) and ablation electrodes (232), the number and positioning of temperature sensors (240) as shown in FIGS. 2B-3 is merely illustrative. In some versions, temperature sensors (240) are operable to sense the temperature of tissue that contacts temperature sensors (240). In some other versions, temperature sensors (240) are operable to sense the temperature of ablation electrodes (232). Regardless of whether temperature sensors (240) sense the temperature of contacted tissue or the temperature of ablation electrodes (232), console (12) may track the sensed tissue temperature in real time and regulate the delivery of electrical energy to ablation electrodes (232) to prevent overheating of tissue by ablation electrodes (232). By way of example only, temperature sensors (240) may come in the form of a thermocouple, such as a negative temperature coefficient (NTC) thermistor or a positive temperature coefficient (PTC) thermistor. Other suitable forms that temperature sensors (240) may take, as well as other suitable uses for temperature sensors (240) in end effector (200), will be apparent to those skilled in the art in view of the teachings herein.

As noted above, and as shown in FIG. 4, a set of reference electrodes (234) are positioned on the second side (216) of panel assembly (210). Such reference electrodes (234) may be utilized in conjunction with mapping electrodes (230) during an EP mapping procedure. For instance, during an EP mapping procedure, mapping electrodes (230) may be placed in contact with tissue in a cardiovascular structure while reference electrodes (234) only contact blood or saline in the cardiovascular structure (i.e., such that reference electrodes (234) do not contact tissue). While mapping electrodes (230) pick up potentials from the contacted tissue, reference electrodes (234) may pick up reference potentials from blood or saline that passes through the cardiovascular structure. Such reference potentials may be used to reduce noise or far field signals, as is known in the art. In the present example, since reference electrodes (234) are only positioned on the side (216) of panel assembly (210) that is opposite from the side (214) on which mapping electrodes (230) are positioned, reference electrodes (234) should not contact tissue while mapping electrodes (230) are contacting tissue.

In some instances, reference electrodes (234) may be used as EP mapping electrodes by applying reference electrodes (234) directly in contact with tissue. In such instances, mapping electrodes (230) may only contact blood or saline in the cardiovascular structure (i.e., such that mapping electrodes (230) do not contact tissue) while reference electrodes (234) are contacting tissue to pick up potentials from the contacted tissue.

In the present example, reference electrodes (234) are positioned in a grid or matrix across second surface (216) of panel assembly (210). Alternatively, the number and positioning of reference electrodes (234) on second surface (216) may be varied in any suitable fashion. In some versions, an annular reference electrode (140) is positioned coaxially about the distal portion of inner shaft (130), as shown in FIG. 2B. This reference electrode (140) may function just like reference electrodes (234) described above; and may form part of end effector (200). Some versions of end effector (200) may include reference electrode (140) instead of including reference electrodes (234). Other versions of end effector (200) may include reference electrodes (234) instead of including reference electrode (140). As yet another variation, each surface (214, 216) of panel assembly (210) may be identically configured. In some such versions, the system need not necessarily differentiate between a set of mapping electrodes (230) and a set of reference electrodes (234). As noted above, electrodes (230, 234) on either surface (214, 216) of panel assembly (210) may function as mapping electrodes while the electrodes (230, 234) on the other surface (214, 216) of panel assembly (210) may function as reference electrodes, depending on which surface (214, 216) is contacting tissue. In cases where the system needs to determine which surface (214, 216) of panel assembly (210) is contacting tissue, this may be accomplished using tissue proximity indications (e.g., impedance measurements at electrodes (230, 234), etc. Still other versions of end effector (200) may include reference electrode (140) and reference electrodes (234).

As shown in FIG. 5, panel assembly (210) of the present example is formed by a plurality of layers (250, 252, 254). In this example, a central layer (250) is formed of a resilient material that provides the bias toward the flattened or expanded configuration. By way of example only, central layer (250) may be formed of nitinol. Alternatively, any other suitable material(s) may be used to form central layer (250). In some versions, central layer (250) is in the form of a single solid sheet that spans across the full length and width of distal portion (212) of panel assembly (210). In some other versions, central layer (250) is provided in the form of one or more strips, a grid, or some other structure.

A first outer layer (252) is positioned on one side of central layer (250) while a second outer layer (254) is positioned on the other side of central layer (250). As shown in FIG. 5, first outer layer (252) presents first surface (214); while second outer layer (254) presents second surface (216). Outer layers (252, 254) are formed of a flexible, non-conductive material in this example. By way of example only, outer layers may be formed of a conventional flex circuit substrate material, such as polyimide, polyether ether ketone, polyester, or any other suitable material as will be apparent to those skilled in the art in view of the teachings herein. Electrodes (230, 232) and temperature sensors (240) (and their corresponding traces) may be applied directly to first outer layer (252) using any of the techniques described herein; or using any other suitable techniques as will be apparent to those skilled in the art in view of the teachings herein. Similarly, electrodes (234) (and their corresponding traces) may be applied directly to second outer layer (254) using any of the techniques described herein; or using any other suitable techniques as will be apparent to those skilled in the art in view of the teachings herein.

By way of example only, electrodes (140, 230, 232, 234) may be formed of nitinol, platinum, gold, or any other suitable material. In some variations of panel assembly (210), where central layer (250) is formed of an electrically conductive material (e.g., nitinol, etc.), central layer (250) may itself effectively form an ablation electrode (232). In such versions, outer layers (252, 254) may be omitted. Alternatively, either or both of outer layers (252, 254) may form one or more openings exposing one or more corresponding regions of central layer (250), with such exposed regions of central layer (250) effectively forming one or more corresponding ablation electrodes (232).

Electrodes (140, 230, 232, 234) may be applied directly to inner shaft (130), first outer layer (252), or second outer layer (254) using a physical vapor deposition (PVD) process. By way of example only, such a PVD process may be carried out in accordance with at least some of the teachings of International Patent Pub. No. WO 2015/117908, entitled "Medical Device for Ablating Tissue Cells and System Comprising a Device of This Type," published Aug. 13, 2015, the disclosure of which is incorporated by reference herein, in its entirety; at least some of the teachings of German Patent Pub. No. 102017130152, entitled "Method for Operating a Multi-Layer Structure," published Jan. 3, 2019, the disclosure of which is incorporated by reference herein, in its entirety; or at least some of the teachings of U.S. Pat. No. 10,061,198, entitled "Method for Producing a Medical Device or a Device with Structure Elements, Method for Modifying the Surface of a Medical Device or of a Device with Structure Elements, Medical Device and Laminated Composite with a Substrate," published Aug. 28, 2018, the disclosure of which is incorporated by reference herein, in its entirety. Other methods may also be employed to deposit electrodes (140, 230, 232, 234), including but not limited to sputter deposition, chemical vapor deposition (CVD), thermal deposition, etc.

Electrodes (140, 230, 232, 234) may include various coatings, if desired. For instance, electrodes (230) may include a coating that is selected to improve the signal-to-noise ratio of signals from electrodes (230). Such coatings may include, but need not be limited to, iridium oxide (IrOx) coating, poly(3,4-ethylenedioxythiophene) (PEDOT) coating, Electrodeposited Iridium Oxide (EIROF) coating, Platinum Iridium (PtIr) coating, or any other suitable coating. Various suitable kinds of coatings that may be used for electrodes (128, 230, 232, 230) will be apparent to those skilled in the art in view of the teachings herein. Electrodes (230, 232) may be arranged in any suitable density across first surface (214). By way of example only, first surface (214) may include from approximately 20 electrodes (230) to approximately 200 electrodes (230). Similarly, first surface (214) may include from approximately 20 electrodes (230) to approximately 200 electrodes (230). Alternatively, any other suitable number of electrodes (230, 232) may be provided. Electrodes (140, 230, 232, 234) may be further constructed and operable in accordance with at least some of the teachings of U.S. Pub. No. 2017/0312022, entitled "Irrigated Balloon Catheter with Flexible Circuit Electrode Assembly," published Nov. 2, 2017, the disclosure of which is incorporated by reference herein, in its entirety.

As noted above, end effector (200) of the present example further includes a set of position sensors (290) located at distal end (218) of panel assembly (210). Position sensors (290) may be applied to first outer surface (252) using any of the processes described herein for applying electrodes (140, 230, 232, 234); or using any other suitable process. While four position sensors (290) are shown, any other suitable number of position sensors (290) may be provided. By way of example only, some other versions may have only one single position sensor (290). Moreover, position sensors (290) may be positioned at any other suitable location(s) on end effector (200). Some variations may provide a position sensor (290) on one or both of outer sheath (122) or inner shaft (130), in addition to or in lieu of providing position sensors (290) on panel assembly (210). In some versions, position sensors (290) may be omitted entirely from end effector (200).

Each position sensor (290) of the present example is operable to generate signals that are indicative of the position and orientation of end effector (200) within the patient (PA). By way of example only, position sensor (290) may be in the form of a wire coil or a plurality of wire coils (e.g., three orthogonal coils) that are configured to generate electrical signals in response to the presence of an alternating electromagnetic field generated by field generators (20). Each position sensor (290) may be coupled with wire, a trace, or any other suitable electrical conduit along or otherwise through catheter (120), thereby enabling signals generated by position sensors (290) to be communicated back through electrical conduits (not shown) in catheter (120) to console (12). Console (12) may process the signals from each position sensor (290) to identify the position of end effector (200) within the patient (PA). Other components and techniques that may be used to generate real-time position data associated with end effector (200) may include wireless triangulation, acoustic tracking, optical tracking, inertial tracking, and the like.

During use of ablation catheter assembly (100), catheter (120) may be advanced to position end effector (200) near a targeted cardiovascular structure (e.g., a chamber of the heart (H), the pulmonary vein, etc.) while end effector (200) is in the non-expanded configuration as shown in FIG. 2A. Outer sheath (122) may then be transitioned to the proximal position shown in FIG. 2B, thereby allowing panel assembly (210) to resiliently unfurl to the expanded state. The physician (PH) may then manipulate catheter assembly (100) to press at least a portion of first surface (214) against tissue of the cardiovascular structure, to thereby place electrodes (230, 232) (and, in some cases, temperature sensors (240)) in contact with the tissue. The physician (PH) may utilize mapping electrodes (230) to map out locations of aberrant conductive activity within the cardiac tissue, with the locations being tracked by position sensors (290). These mapped sites may be displayed on display (18). The physician (PH) may then urge ablation electrodes (232) against the tissue at these sites and thereby utilize ablation electrodes (232) to ablate the sites of aberrant conductive activity within the cardiac tissue. In some cases, the mapping procedure and the ablation procedure may be carried out in separate patient (PA) visits. In such cases, real time data from position sensors (290) may be used to guide ablation electrodes (232) back to the originally mapped sites of aberrant conductive activity within the cardiac tissue. In some other cases, the mapping procedure and the ablation procedure may be carried out in the same patient (PA) visit, without catheter (120) needing to be removed from the patient (PA) between the mapping procedure and the ablation procedure. Even in these scenarios, real time data from position sensors (290) may be used to assist in appropriately positioning ablation electrodes (232) at the mapped sites of aberrant conductive activity within the cardiac tissue.

III. Examples of Alternative End Effector Configurations

The above described configuration of end effector (200) is just one merely illustrative example. End effector (200) may be modified in numerous ways. Several examples of such modifications will be described in greater detail below with reference to FIGS. 6-11.

As noted above, it may be desirable to avoid contact between each reference electrode (234) and tissue during an EP mapping procedure. Avoiding such contact will enable reference electrodes (234) to only pick up reference potentials from blood or saline that passes through the targeted cardiovascular structure, thereby allowing signals from reference electrodes (234) to be used to reduce noise or far field signals, which may in turn provide better resolution on electrocardiogram signals picked up through mapping electrodes (230).

Figure 6:
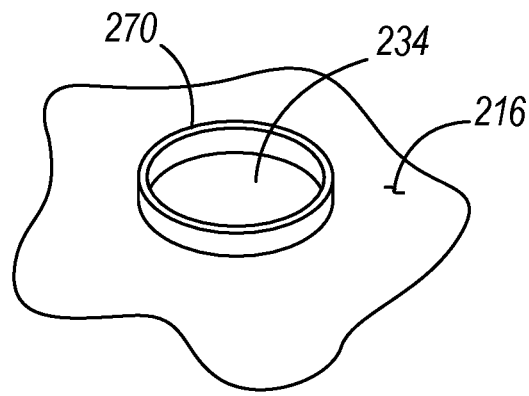
FIG. 6 depicts a perspective view of an example of a reference electrode feature that may be incorporated into the panel assembly of FIG. 3.

FIG. 6 shows one example of a feature that may be used to reduce the risk of inadvertent contact between reference electrodes (234) and tissue. In particular, FIG. 6 shows a wall (270) surrounding reference electrode (234). Each electrode (234) may have an associated wall (270). By way of example only, wall (270) may protrude from second surface (216) at a height from approximately 20 microns to approximately 2 mm. Wall (270) may be formed in numerous different ways. For instance, additive manufacturing (e.g., photolithography, etc.) or subtractive manufacturing (e.g., etching into the substrate, etc.) may be used.

Figure 7:
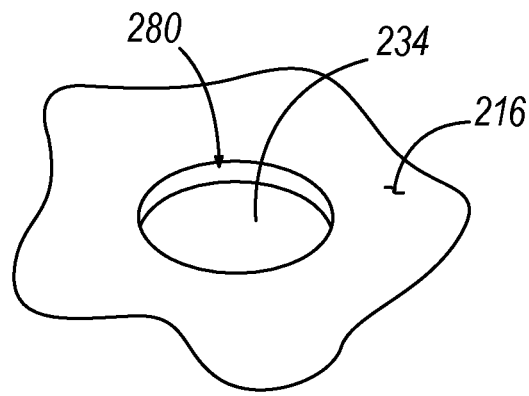
FIG. 7 depicts a perspective view of another example of a reference electrode feature that may be incorporated into the panel assembly of FIG. 3.

FIG. 7 shows another example of a feature that may be used to reduce the risk of inadvertent contact between reference electrodes (234) and tissue. In particular, FIG. 7 shows reference electrode (234) being positioned in a recess (280) formed in second surface (216). Such a recess (280) may position reference electrode (234) at a depth from approximately 20 microns to approximately 2 mm relative to second surface (216). Recess (280) may be formed in numerous different ways. For instance, additive manufacturing (e.g., photolithography, etc.), subtractive manufacturing (e.g., etching into the substrate, etc.), or overmolding of a flexible polymer (e.g., silicone) may be used.

Figure 8:
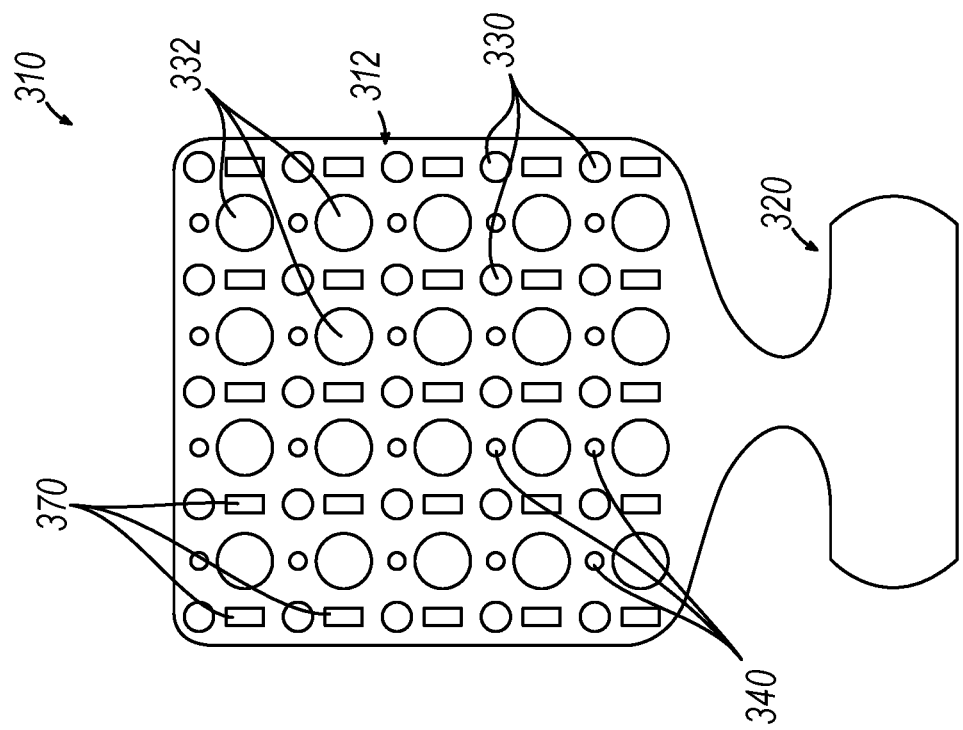
FIG. 8 depicts a top plan view of another example of a panel assembly that may be incorporated into the end effector of FIG. 2A.

In some instances, it may be desirable to permit fluid to be communicated through panel assembly (210). By way of example only, providing openings through panel assembly (210) may prevent naturally flowing blood from causing panel assembly (210) to undesirably flex while panel assembly (210) is being positioned within the targeted anatomical region of the cardiovascular system. In addition, or in the alternative, such openings may promote irrigation fluid reaching the interface between tissue and ablation electrodes (232). In view of the foregoing, FIG. 8 shows an example of an alternative panel assembly (310) that is substantially similar to panel assembly (210), except that panel assembly (310) of this example includes a plurality of openings (370) formed therethrough. Like panel assembly (210), panel assembly (310) of this example includes a distal portion (312) and a proximal portion (320), with distal portion (312) including mapping electrodes (330), ablation electrodes (332), and temperature sensors (340). Panel assembly (310) may also include reference electrodes like reference electrodes (234); and position sensors like position sensors (290). Openings (370) of this example are formed through both opposing surfaces of distal portion (312), thereby allowing fluids to pass through distal portion (312). While openings (370) are shown as being rectangular in shape, openings (370) may instead have any other suitable shape. Openings (370) may also be positioned in any other suitable locations along panel assembly (310).

As another merely illustrative variation, panel assembly (210) may be formed as a mesh that defines openings therethrough, such that the mesh material may serve as a substrate for electrodes (230, 232, 234) and temperature sensors (240). Such a mesh may allow fluid to pass through panel assembly (210); and may also provide a resilient bias urging panel assembly (210) to assume the flattened configuration shown in FIG. 2B. In some versions where panel assembly (210) is formed by a mesh, such a mesh may be extensible to allow panel assembly (210) to expand further beyond the configuration shown in 2B as described below. Such a mesh may also be contractible to allow for panel assembly (210) to shrink in the lateral dimension when collapsing into outer sheath (122).

Figure 9:
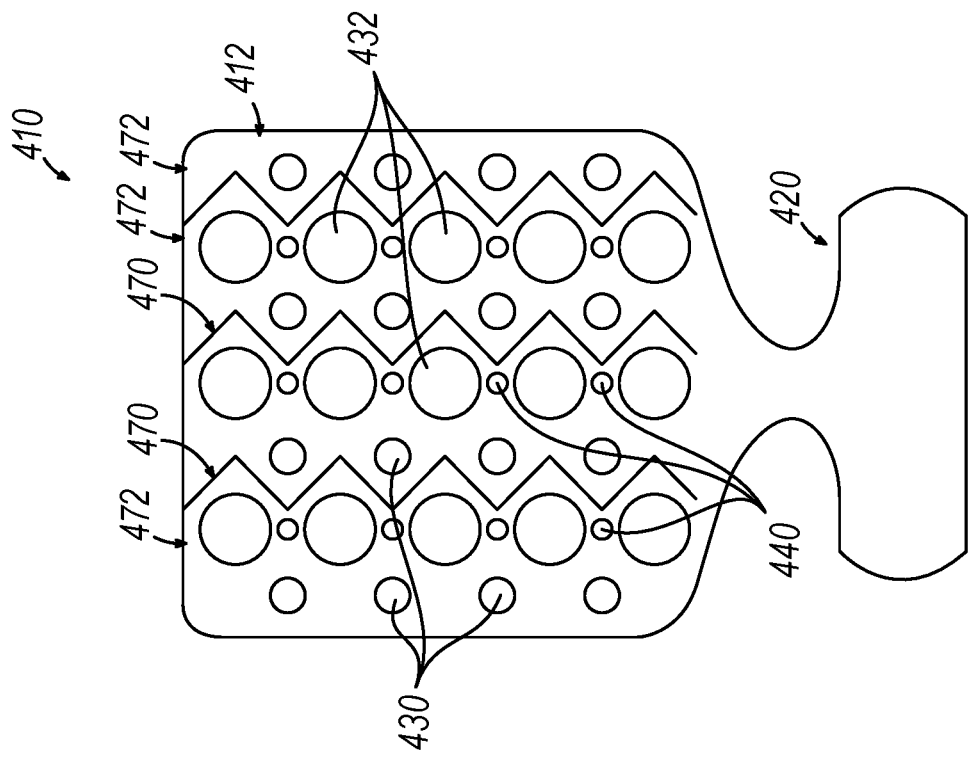
FIG. 9 depicts a top plan view of another example of a panel assembly that may be incorporated into the end effector of FIG. 2A.

In some instances, it may be desirable to configured panel assembly (210) to enable panel assembly (210) to expand further beyond the configuration shown in FIG. 2B. This may include scenarios where panel assembly (210) is mounted to an actively expandable body (e.g., as described below with reference to FIGS. 10-11) and in other scenarios where panel assembly (210) is not mounted to an actively expandable body. For instance, allowing panel assembly (210) to expand further beyond the configuration shown in FIG. 2B may allow panel assembly to more easily conform to contours of anatomical structures; or may otherwise promote better contact between electrodes (230, 232) and tissue. In view of the foregoing, FIG. 9 shows an example of an alternative panel assembly (410) that is substantially similar to panel assembly (210), except that panel assembly (410) of this example includes a plurality of cuts (470) formed therethrough. Like panel assembly (210), panel assembly (410) of this example includes a distal portion (412) and a proximal portion (420), with distal portion (412) including mapping electrodes (430), ablation electrodes (432), and temperature sensors (440). Panel assembly (410) may also include reference electrodes like reference electrodes (234); and position sensors like position sensors (290). Cuts (470) of this example are formed through both opposing surfaces of distal portion (412), thereby allowing distal portion (312) to form strips (472) that fan out from each other or otherwise separate from each other along various dimensions. While cuts (470) are shown as having a zigzag shape, cuts (470) may instead have any other suitable shape. Similarly, while cuts (470) are shown as being oriented generally longitudinally along distal portion (412), cuts (470) may instead be oriented generally laterally; or may be positioned and oriented in any other suitable fashion along panel assembly (410).

Figure 10:
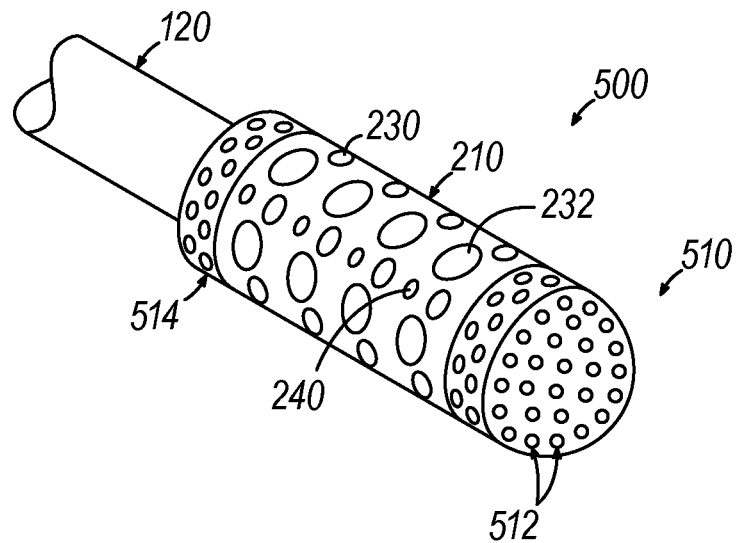
FIG. 10 depicts a perspective view of another example of an end effector that may be incorporated into the catheter assembly of FIG. 1.

In some instances, it may be desirable to secure a panel assembly such as any of the above-described panel assemblies (210, 310, 410) to an inflatable body. Such an inflatable body may assist in expanding panel assembly (210, 310, 410) after panel assembly (210, 310, 410) is exposed from sheath (122). Such an inflatable body may further provide additional structural integrity to panel assembly (210, 310, 410), thereby helping to ensure appropriate contact between electrodes (230, 232, 330, 332, 430, 432) and tissue when panel assembly (210, 310, 410) is urged against tissue. FIGS. 10-11 show two examples of ways in which an end effector (500, 600) may be formed by securing panel assembly (210) to an inflatable body (510, 610). End effectors (500, 600) of these examples are secured to the distal end of a catheter (120) and are generally operable like end effector (200) described above. While panel assembly (210) is shown and described in these examples, panel assemblies (310, 410) and variations thereof may be used instead of panel assembly (210). Moreover, while inflatable bodies (510, 610) are shown and described in these examples, other variations may utilize mechanically expandable bodies that do not require inflation for expansion.

As shown in FIG. 10, end effector (500) is formed by panel assembly (210) and an inflatable body (510). Inflatable body (510) is in the form of a membrane that defines a plurality of openings (512). Inflatable body (510) of this example has a cylindraceous shape in the expanded state, with panel assembly (210) being wrapped about the longitudinally extending portion (514) of inflatable body (510). Openings (512) are large enough to allow fluid to pass through openings (512) while being small enough to allow inflatable body (510) to achieve and maintain an expanded state when inflatable body is filled with an inflation fluid (e.g., saline, etc.). In some versions, the same fluid that is used to inflate inflatable body (510) is expelled through openings (512) to provide irrigation at a targeted site in the patient (PA). For instance, fluid from fluid source (42) may be expelled through openings (512). In addition, or in the alternative, the blood of the patient (PA) may enter the interior of end effector (500) via openings (512) to reach reference electrodes (234), which may be exposed within the interior of inflatable body (510).

As another merely illustrative alternative, inflatable body (510) may include two layers, with a fluid-tight space between the layers that receives an inflation fluid, such that the inflation fluid is not expelled through openings (512). In some such versions, irrigation fluid from fluid source (42) is communicated to the interior of inflatable body (510) via fluid conduit (40); and is expelled out through openings (512). It should also be understood that openings (512) may be omitted in some versions. By way of further example only, inflatable body (510) may be made of a non-extensible material. Alternatively, inflatable body (510) may be made of an extensible material. In some variations, body (510) lacks openings (512). In such versions (and in versions where openings (512) are present), irrigation fluid may be expelled from end effector (500) via one or more irrigation ports provided by catheter (120).

In some scenarios, the cylindraceous configuration of inflatable body (510) may be particularly useful when end effector (500) is positioned in a generally tubular anatomical structure, such as a pulmonary vein. For instance, the curvature of longitudinally extending portion (514) of inflatable body (510) may promote contact between electrodes (230, 232) and the curved inner wall of the pulmonary vein.

FIG. 11 shows another end effector (600) that is formed by panel assembly (210) and an inflatable body (610). Inflatable body (610) is in the form of a membrane that defines a plurality of openings (612). Inflatable body (610) of this example has a generally flat rectangular shape in the expanded state, with one panel assembly (210) being positioned on one broad face (620) of inflatable body (610). In some versions, another panel assembly (210) is positioned on the other, opposite broad face (622) of inflatable body (610). Openings (612) are large enough to allow fluid to pass through openings (612) while being small enough to allow inflatable body (610) to achieve and maintain an expanded state when inflatable body is filled with an inflation fluid (e.g., saline, etc.). In some versions, the same fluid that is used to inflate inflatable body (610) is expelled through openings (612) to provide irrigation at a targeted site in the patient (PA). For instance, fluid from fluid source (42) may be expelled through openings (612). In addition, or in the alternative, the blood of the patient (PA) may enter the interior of end effector (600) via openings (612) to reach reference electrodes (234), which may be exposed within the interior of inflatable body (610).

As another merely illustrative alternative, inflatable body (610) may include two layers, with a fluid-tight space between the layers that receives an inflation fluid, such that the inflation fluid is not expelled through openings (612). In some such versions, irrigation fluid from fluid source (42) is communicated to the interior of inflatable body (610) via fluid conduit (40); and is expelled out through openings (612). It should also be understood that openings (612) may be omitted in some versions. By way of further example only, inflatable body (610) may be made of a non-extensible material. Alternatively, inflatable body (610) may be made of an extensible material. In some variations, body (610) lacks openings (612). In such versions (and in versions where openings (612) are present), irrigation fluid may be expelled from end effector (600) via one or more irrigation ports provided by catheter (120).

In some scenarios, the generally flat rectangular configuration of inflatable body (610) may be particularly useful when end effector (600) is positioned in an anatomical structure that has generally flat inner walls, such as chambers of the heart (H). For instance, the flatness of broad face (620) of inflatable body (610) may promote contact between electrodes (230, 232) and the generally flat inner wall of a chamber of the heart (H).

While end effectors (500, 600) are shown with inflatable bodies (510, 610) having cylindraceous and generally flat rectangular configurations, panel assemblies (210, 310, 410) may alternatively be secured to inflatable bodies having various other kinds of configurations as will be apparent to those skilled in the art in view of the teachings herein.

While panel assembly (210) is described above as incorporating position sensors (290) in distal portion (212) of panel assembly (210), other variations may instead incorporate position sensors (290) in proximal end (220) of panel assembly (210). FIGS. 15-18 show examples of how this may be carried out. In particular, FIGS. 15-16 show a panel assembly (700) that includes a distal portion (710) and a proximal tab portion (720), with a narrowed region (712) separating distal portion (710) from proximal tab portion (720). Distal portion (710) may be configured and operable like distal portion (212, 312, 412) described above; and may thus include electrodes (230, 232, 234, 330, 332, 430, 432), temperature sensors (240, 340, 440), openings (370), cuts (470), etc.

Panel assembly (700) of FIGS. 15-16 includes a two-axis ($CA_1$, $CA_2$) position sensor assembly integrated into proximal tab portion (720). Proximal tab portion (720) includes a first laterally extending tab (722) and a second laterally extending tab (724). A first coil (730) and a second coil (732) are positioned on second laterally extending tab (724). In some other versions, at least one coil (730, 732) is positioned on first laterally extending tab (722) or elsewhere on proximal tab portion (720). By way of example only, coils (730, 732) may be printed onto proximal tab portion (720) as part of a flex circuit construction or may be otherwise integrated proximal tab portion (720) using any suitable techniques as will be apparent to those skilled in the art in view of the teachings herein.

Each coil (730, 732) encircles a respective axis ($CA_1$, $CA_2$) at the center of the corresponding coil (730, 732). Each coil (730, 732) is operable to generate signals that are indicative of the position and orientation of panel assembly (700) within the patient (PA). By way of example only, coils (730, 732) may be configured to generate electrical signals in response to the presence of an alternating electromagnetic field generated by field generators (20). Each coil (730, 732) may be coupled with wire, a trace, or any other suitable electrical conduit along or otherwise through catheter (120), thereby enabling signals generated by coils (730, 732) to be communicated back through electrical conduits (not shown) in catheter (120) to console (12). Console (12) may process the signals from each coil (730, 732) to identify the position of panel assembly (700) within the patient (PA).

FIG. 16 shows an example of how proximal tab portion (720) may be rolled to assist in securing panel assembly (700) to distal end (132) of inner shaft (130) as described above. In the present example, tabs (722, 724) overlap when proximal tab portion (720) is in this rolled configuration. With proximal tab portion (720) in the rolled configuration, the axes ($CA_1$, $CA_2$) of coils (730, 732) are both orthogonal to the longitudinal axis (LA) of the end effector that incorporates panel assembly (700). The axes ($CA_1$, $CA_2$) of coils (730, 732) are also neither aligned with each other nor parallel with each other. In some versions, the axes ($CA_1$, $CA_2$) of coils (730, 732) are orthogonal to each other when proximal tab portion (720) is in the rolled configuration shown in FIG. 16 and secured to distal end (132) of inner shaft (130), though such an orthogonal relationship is not necessarily required.

As also shown in FIG. 16, proximal tab portion (720) defines a passageway (740) when proximal tab portion (720) is in the rolled configuration. By way of example only, this passageway (740) may accommodate other instrumentation, such as a guidewire, another catheter, etc. By way of further example only, passageway (740) may provide a path for expulsion of irrigating fluid (e.g., saline, etc.). Other suitable ways in which passageway (740) may be used will be apparent to those skilled in the art in view of the teachings herein. Alternatively, passageway (740) need not necessarily be used for anything.

In some variations of panel assembly (700), it may be desirable to provide an additional position sensing coil axis ($CA_3$). FIGS. 17-18 show an example of how such a variation may be carried out. In particular, FIGS. 17-18 show a panel assembly (800) that includes a distal portion (810) and a proximal tab portion (820), with a narrowed region (812) separating distal portion (810) from proximal tab portion (820). Distal portion (810) may be configured and operable like distal portion (212, 312, 412) described above; and may thus include electrodes (230, 232, 234, 330, 332, 430, 432), temperature sensors (240, 340, 440), openings (370), cuts (470), etc.

Panel assembly (800) of FIGS. 17-18 includes a three-axis ($CA_1$, $CA_2$, $CA_3$) position sensor assembly integrated into proximal tab portion (820). Proximal tab portion (820) includes a first laterally extending tab (822), a second laterally extending tab (824), and a distally extending tab (826) projecting from second laterally extending tab (824). A first coil (830) and a second coil (832) are positioned on second laterally extending tab (824). A third coil (834) is positioned on distally extending tab (826). In some other versions, at least one coil (830, 832, 834) is positioned on first laterally extending tab (822) or elsewhere on proximal tab portion (820). By way of example only, coils (830, 832, 834) may be printed onto proximal tab portion (820) as part of a flex circuit construction or may be otherwise integrated proximal tab portion (820) using any suitable techniques as will be apparent to those skilled in the art in view of the teachings herein.

Each coil (830, 832, 834) encircles a respective axis ($CA_1$, $CA_2$, $CA_3$) at the center of the corresponding coil (830, 832, 834). Each coil (830, 832, 834) is operable to generate signals that are indicative of the position and orientation of panel assembly (800) within the patient (PA). By way of example only, coils (830, 832, 834) may be configured to generate electrical signals in response to the presence of an alternating electromagnetic field generated by field generators (20). Each coil (830, 832, 834) may be coupled with wire, a trace, or any other suitable electrical conduit along or otherwise through catheter (120), thereby enabling signals generated by coils (830, 832, 834) to be communicated back through electrical conduits (not shown) in catheter (120) to console (12). Console (12) may process the signals from each coil (830, 832, 834) to identify the position of panel assembly (800) within the patient (PA).

FIG. 18 shows an example of how proximal tab portion (820) may be rolled to assist in securing panel assembly (800) to distal end (132) of inner shaft (130) as described above. In the present example, tabs (822, 824) overlap when proximal tab portion (820) is in this rolled configuration. With proximal tab portion (820) in the rolled configuration, the axes ($CA_1$, $CA_2$) of coils (830, 832) are both orthogonal to the longitudinal axis (LA) of the end effector that incorporates panel assembly (800). The axes ($CA_1$, $CA_2$) of coils (830, 832) are also neither aligned with each other nor parallel with each other. In some versions, the axes ($CA_1$, $CA_2$) of coils (830, 832) are orthogonal to each other when proximal tab portion (820) is in the rolled configuration shown in FIG. 18 and secured to distal end (132) of inner shaft (130), though such an orthogonal relationship is not necessarily required.

As also shown in FIG. 18, distally extending tab (826) is folded over a passageway (840) defined by rolled laterally extending tabs (822, 824). This positions the axis ($CA_3$) of coil (834) parallel with the longitudinal axis (LA) of the end effector that incorporates panel assembly (800). This also positions the axis ($CA_3$) of coil (834) orthogonal to the axes ($CA_1$, $CA_2$) of coils (830, 832). The additional sensing axis ($CA_3$) provided by coil (834) may generate additional position and orientation data associated with panel assembly (800), as compared with the position data generated by the two-axis ($CA_1$, $CA_2$) sensing assembly defined by coils (730, 732) of panel assembly (700).

In some versions, distally extending tab (826) defines an opening (not shown) within the central region of coil (834). Such an opening may accommodate other instrumentation, such as a guidewire, another catheter, etc. By way of further example only, an opening formed through distally extending tab (826) within the central region of coil (834) may provide a path for expulsion of irrigating fluid (e.g., saline, etc.). Other suitable ways in which such an opening may be used will be apparent to those skilled in the art in view of the teachings herein. Alternatively, an opening need not necessarily be formed through distally extending tab (826).

Even if panel assembly (700, 800) includes coils (730, 732, 830, 832, 834) to provide position sensing, distal portion (710, 810) may also include one or more position sensors (e.g., like position sensors (290) of panel assembly (210).

Figure 20:
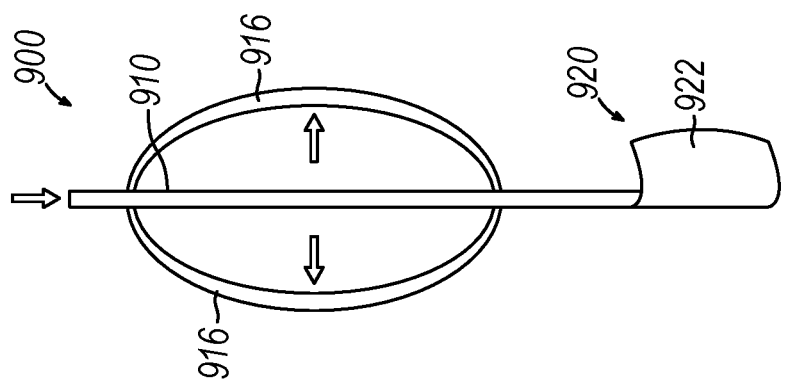
FIG. 20 depicts a side elevation view of the panel component of FIG. 19 in an expanded configuration.
Figure 19:
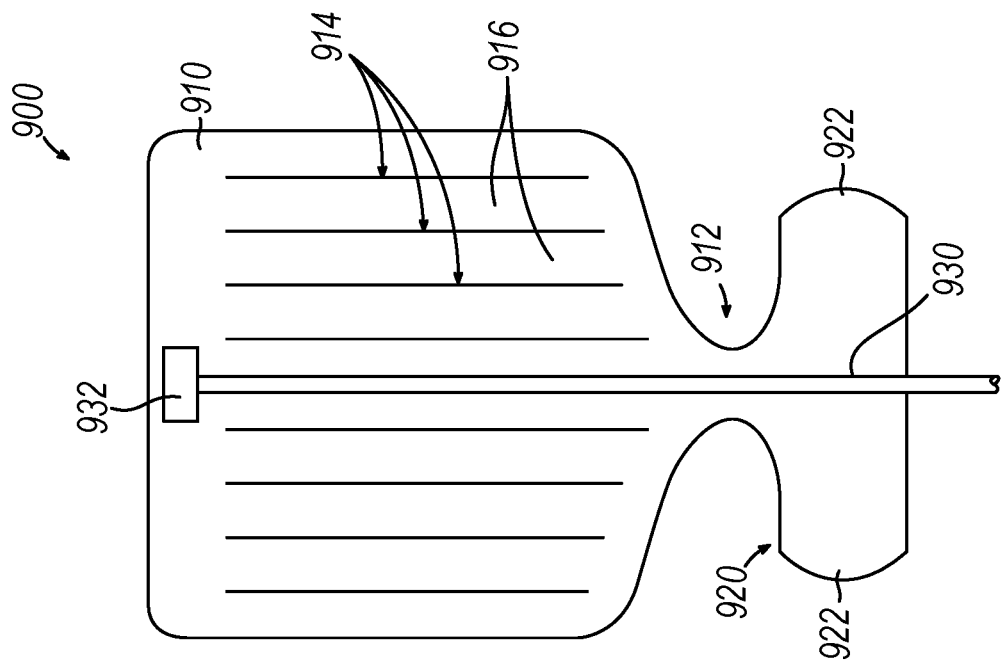
FIG. 19 depicts a depicts a top plan view of another example of a panel component that may be incorporated into any of the panel assemblies described herein.

In some variations, a pull-wire or other actuator may be utilized to further expand a panel assembly. FIGS. 19-20 show an example of how this may be achieved. In particular, FIGS. 19-20, show a panel assembly (900) that includes a distal portion (910) and a proximal tab portion (920), with a narrowed region (912) separating distal portion (910) from proximal tab portion (920). Distal portion (910) may be configured and operable like distal portion (212, 312, 412) described above; and may thus include electrodes (230, 232, 234, 330, 332, 430, 432), temperature sensors (240, 340, 440), openings (370), cuts (470), etc. Proximal tab portion (920) includes a pair of laterally extending tabs (922). By way of example only, tabs (922) may be configured and operable like tabs (722, 724, 822, 824, 826).

Panel assembly (900) of this example further includes a plurality of slits (914) formed through distal portion (910). Slits (914) effectively define a plurality of beam regions (916) between slits (914). While slits (914) are shown as straight lines in this example, slits (914) may instead have a zigzag configuration, a wave-like configuration, or any other suitable configuration. A pull-wire (930) is secured to a distal region of distal portion (910) via an anchor (932). In some other versions, a band, strip, or other actuating member is used in lieu of pull-wire (930).

Panel assembly (900) is configured to transition from a flat configuration as shown in FIG. 19 to a further expanded configuration as shown in FIG. 20 in response to proximal retraction of pull-wire (930). When pull-wire (930) is retracted proximally, with proximal regions of beam regions (916) being effectively grounded mechanically, beam regions (916) may buckle outwardly in opposing directions as shown in FIG. 20. In some versions, panel assembly (900) may include selectively configured and positioned reinforcement features that allow this outward buckling of beam regions (916) while preventing the rest of panel assembly (900) from simply collapsing proximally when pull-wire (930) is retracted proximally.

Panel assembly (900) may thus be operable to transition from a non-expanded configuration (e.g., similar to what is shown in FIG. 2A) when panel assembly (900) is contained within an outer sheath (122); to a first expanded configuration (e.g., as shown in FIG. 19) when panel assembly (900) is exposed relative to outer sheath (122); and then to a second expanded configuration (e.g., as shown in FIG. 20) when pull-wire (930) is retracted proximally. In this second expanded configuration, panel assembly (900) may be more likely to promote contact between electrodes (230, 232, 234, 330, 332, 430, 432) on panel assembly (900) and adjacent tissue.

IV. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a catheter, at least a portion of the catheter being sized and configured to fit within a lumen of a cardiovascular system; and (b) an end effector positioned at a distal end of the catheter, the end effector comprising: (i) a panel, the panel being biased to assume an expanded configuration, (ii) a plurality of mapping electrodes positioned on a first surface of the panel, the mapping electrodes being configured to sense electrical potentials in tissue contacting the mapping electrodes, and (iii) a plurality of ablation electrodes positioned on the first surface of the panel, the ablation electrodes being operable to ablate tissue contacting the ablation electrodes.

Example 2

The apparatus of Example 1, the panel including a distal portion biased to assume a generally flat shape in the expanded configuration.

Example 3

The apparatus of any one or more of Examples 1 through 2, the panel including a distal portion having a generally rectangular shape.

Example 4

The apparatus of any one or more of Examples 1 through 3, the catheter including an outer sheath, the outer sheath and end effector being configured to transition between a first state and a second state, the end effector being contained within the outer sheath in the first state, the end effector being exposed relative to the outer sheath in the second state.

Example 5

The apparatus of Example 4, the panel being configured to be in a non-expanded configuration within the outer sheath in the first state.

Example 6

The apparatus of Example 5, the panel being configured to be in a rolled non-expanded configuration within the outer sheath in the first state.

Example 7

The apparatus of any one or more of Examples 4 through 6, the panel including a proximal portion with a camming feature configured to cooperate with a distal end of the other sheath to thereby urge the panel from the expanded configuration to the non-expanded configuration in response to the outer sheath and end effector transitioning from the second state to the first state.

Example 8

The apparatus of Example 7, the camming feature comprising a tapered proximally facing edge of the panel.

Example 9

The apparatus of any one or more of Examples 7 through 8, the camming feature comprising a concave curved portion of a proximal region of the panel.

Example 10

The apparatus of any one or more of Examples 1 through 9, the panel being resiliently biased to assume the expanded configuration.

Example 11

The apparatus of Example 10, the panel including a resilient material biasing the panel to assume the expanded configuration.

Example 12

The apparatus of Example 11, the resilient material comprising nitinol.

Example 13

The apparatus of any one or more of Examples 11 through 12, the panel including a plurality of layers, at least one of the layers comprising the resilient material.

Example 14

The apparatus of Example 13, the layers further including a non-conductive layer, at least one of the mapping electrodes and at least one of the ablation electrodes being positioned on a first side of the non-conductive layer, the resilient material being positioned on a second side of the non-conductive layer.

Example 15

The apparatus of any one or more of Examples 1 through 14, the end effector further comprising an inflatable member, the panel being secured to the inflatable member.

Example 16

The apparatus of Example 15, the inflatable member being configured to bias the panel to assume the expanded configuration.

Example 17

The apparatus of any one or more of Examples 15 through 16, the inflatable member defining a plurality of openings, the openings being configured to allow communication of fluid between an interior region of the inflatable member and the exterior region of the inflatable member.

Example 18

The apparatus of any one or more of Examples 15 through 17, the inflatable member being configured to define a cylindraceous shape in an inflated state.

Example 19

The apparatus of any one or more of Examples 15 through 17, the inflatable member being configured to define a generally flat rectangular shape in an inflated state.

Example 20

The apparatus of any one or more of Examples 1 through 19, the end effector further comprising at least one reference electrode.

Example 21

The apparatus of Example 20, the at least one reference electrode comprising one or more reference electrodes positioned on a second surface of the panel, the second surface being opposite to the first surface.

Example 22

The apparatus of Example 21, the second surface of the panel including a feature to prevent the one or more reference electrodes from contacting tissue adjacent to the second surface.

Example 23

The apparatus of Example 22, the feature to prevent the one or more reference electrodes from contacting tissue adjacent to the second surface comprising one or more walls surrounding the or more reference electrodes, the one or more walls protruding from the second surface.

Example 24

The apparatus of any one or more of Examples 22 through 23, the feature to prevent the one or more reference electrodes from contacting tissue adjacent to the second surface comprising one or more recesses formed in the second surface, each of the one or more reference electrodes being positioned in a corresponding recess of the one or more recesses.

Example 25

The apparatus of any one or more of Examples 20 through 24, the catheter including a shaft, the at least one electrode comprising one or more electrodes positioned on the shaft.

Example 26

The apparatus of any one or more of Examples 1 through 25, the mapping electrodes being arranged in a matrix of rows and columns along the first surface.

Example 27

The apparatus of any one or more of Examples 1 through 26, the ablation electrodes being arranged in a matrix of rows and columns along the first surface.

Example 28

The apparatus of any one or more of Examples 1 through 25, the mapping electrodes being arranged in a first matrix of rows and columns along the first surface, the ablation electrodes being arranged in a second matrix of rows and columns along the first surface, the second matrix being offset from the first matrix.

Example 29

The apparatus of any one or more of Examples 1 through 28, the end effector further comprising a plurality of temperature sensors.

Example 30

The apparatus of Example 29, the temperature sensors comprising thermocouples.

Example 31

The apparatus of Example 30, the thermocouples comprising thermistors.

Example 32

The apparatus of any one or more of Examples 1 through 31, the panel further defining a plurality of openings through the panel.

Example 33

The apparatus of Example 32, the openings being arranged in a matrix.

Example 34

The apparatus of any one or more of Examples 1 through 33, the panel defining a plurality of cuts separating a plurality of strips, the strips being movable relative to each other at the cuts.

Example 35

The apparatus of Example 34, the cuts defining zigzag patterns.

Example 36

An apparatus comprising: (a) a catheter, at least a portion of the catheter being sized and configured to fit within a lumen of a cardiovascular system; and (b) an end effector positioned at a distal end of the catheter, the end effector comprising: (i) a panel defining a first surface and a second surface, the second surface being opposite to the first surface, (ii) a plurality of mapping electrodes arranged in a first grid along the first surface of the panel, the mapping electrodes being configured to sense electrical potentials in tissue contacting the mapping electrodes, and (iii) a plurality of ablation electrodes arranged in a second grid along the first surface of the panel, the ablation electrodes being operable to ablate tissue contacting the ablation electrodes, the second grid being offset from the first grid.

Example 37

The apparatus of Example 36, the end effector further comprising at least one reference electrode positioned on the second surface.

Example 38

The apparatus of Example 37, the at least one reference electrode comprising a plurality of reference electrodes arranged in a grid along the second surface.

Example 39

An apparatus comprising: (a) a catheter, at least a portion of the catheter being sized and configured to fit within a lumen of a cardiovascular system; and (b) an end effector positioned at a distal end of the catheter, the end effector comprising: (i) a panel defining a first surface and a second surface, the second surface being opposite to the first surface, (ii) a plurality of mapping electrodes positioned along the first surface of the panel, the mapping electrodes being configured to sense electrical potentials in tissue contacting the mapping electrodes, (iii) a plurality of ablation electrodes positioned along the first surface of the panel, the ablation electrodes being operable to ablate tissue contacting the ablation electrodes, the second grid being offset from the first grid, and (iv) one or more reference electrodes positioned on the second surface of the panel.

Example 40

An apparatus comprising: (a) a catheter, at least a portion of the catheter being sized and configured to fit within a lumen of a cardiovascular system, the catheter including an outer sheath; and (b) an end effector positioned at a distal end of the catheter, the outer sheath being operable to transition between a distal position and a proximal position, the end effector comprising: (i) a panel defining a first surface and a second surface, the second surface being opposite to the first surface, the panel being configured to assume the rolled configuration within the outer sheath when the outer sheath is in the distal position, the panel being configured to assume a generally flat configuration when the outer sheath is in the proximal position, (ii) a plurality of mapping electrodes positioned along the first surface of the panel, the mapping electrodes being configured to sense electrical potentials in tissue contacting the mapping electrodes, (iii) a plurality of ablation electrodes positioned along the first surface of the panel, the ablation electrodes being operable to ablate tissue contacting the ablation electrodes, the second grid being offset from the first grid.

V. Miscellaneous

Any of the instruments described herein may be cleaned and sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, hydrogen peroxide, peracetic acid, and vapor phase sterilization, either with or without a gas plasma, or steam.

It should be understood that any of the examples described herein may include various other features in addition to or in lieu of those described above. By way of example only, any of the examples described herein may also include one or more of the various features disclosed in any of the various references that are incorporated by reference herein in its entirety.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein in its entirety is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein in its entirety, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a catheter having a central longitudinal axis, at least a portion of the catheter being sized and configured to fit within a lumen of a cardiovascular system; and
   (b) an end effector positioned at a distal end of the catheter, the end effector comprising:
      (i) a panel comprising a proximal tab portion, a distally extending portion, and a transition portion between the proximal tab portion and the distally extending portion, the transition portion being narrower than both the proximal tab portion and the distally extending portion, the distally extending portion being biased to assume an expanded configuration, the proximal tab portion comprising two laterally extending ears that are rolled to form a generally cylindrical proximal tab that is fixedly secured along an inner perimeter of a distal end of the catheter such that when in the expanded configuration the distally extending portion extends laterally offset from the central longitudinal axis of the catheter, the proximal tab defining an opening configured to pass fluid from the catheter to an area outside of the distal end of the catheter and proximal of the distally extending portion of the panel,
      (ii) a plurality of mapping electrodes positioned on a first surface of the distally extending portion of the panel, the mapping electrodes being configured to sense electrical potentials in tissue contacting the mapping electrodes, and
      (iii) a plurality of ablation electrodes positioned on the first surface of the distally extending portion of the panel, the ablation electrodes being operable to ablate tissue contacting the ablation electrodes.

2. The apparatus of claim 1, the distally extending portion of the panel being biased to assume a generally flat shape in the expanded configuration.

3. The apparatus of claim 1, the distally extending portion of the panel having a generally rectangular shape.

4. The apparatus of claim 1, the catheter including an outer sheath, the outer sheath and end effector being configured to transition between a first state and a second state, the end effector being contained within the outer sheath in the first state, the end effector being exposed relative to the outer sheath in the second state.

5. The apparatus of claim 4, the panel comprising a camming feature configured to cooperate with a distal end of the outer sheath to thereby urge the panel from the expanded configuration to a non-expanded configuration in response to the outer sheath and end effector transitioning from the second state to the first state.

6. The apparatus of claim 1, the distally extending portion of the panel being resiliently biased to assume the expanded configuration.

7. The apparatus of claim 6, the distally extending portion of the panel including a resilient material biasing the distally extending portion of the panel to assume the expanded configuration.

8. The apparatus of claim 7, the distally extending portion of the panel including a plurality of layers, at least one of the layers comprising the resilient material.

9. The apparatus of claim 8, the plurality of layers further including a non-conductive layer, at least one of the mapping electrodes and at least one of the ablation electrodes being positioned on a first side of the non-conductive layer, the resilient material being positioned on a second side of the non-conductive layer.

10. The apparatus of claim 1, the end effector further comprising an inflatable member, the panel being secured to the inflatable member, the inflatable member being configured to bias the panel to assume the expanded configuration.

11. The apparatus of claim 10, the inflatable member being configured to define a cylindraceous shape in an inflated state.

12. The apparatus of claim 10, the inflatable member being configured to define a generally flat rectangular shape in an inflated state.

13. The apparatus of claim 1, the end effector further comprising one or more reference electrodes positioned on a second surface of the distally extending portion of the panel, the second surface being opposite to the first surface.

14. The apparatus of claim 13, the second surface of the distally extending portion of the panel including a feature to prevent the one or more reference electrodes from contacting tissue adjacent to the second surface.

15. The apparatus of claim 14, the feature to prevent the one or more reference electrodes from contacting tissue comprising:
   a protruding wall generally surrounding a respective reference electrode and protruding from the second surface; or a recess in the second surface in which the respective reference electrode sits.

16. The apparatus of claim 1, the mapping electrodes being arranged in a first matrix of rows and columns along the first surface, the ablation electrodes being arranged in a second matrix of rows and columns along the first surface, the second matrix being offset from the first matrix.

17. The apparatus of claim 1, the end effector further comprising a plurality of temperature sensors.

18. The apparatus of claim 1, the distally extending portion of the panel further comprising a plurality of openings through the panel.

19. The apparatus of claim 1, the distally extending portion of the panel comprising a plurality of cuts through the first surface and an opposing second surface of the distally extending portion of the panel such that the plurality of cuts separate the distally extending portion of the panel into a plurality of strips, the strips being movable relative to each other at the cuts.

20. The apparatus of claim 19, the strips of the plurality of strips being configured to fan out from each other or separate from each other along multiple dimensions.

* * * * *